(12) United States Patent
Baxter et al.

(10) Patent No.: US 11,766,538 B2
(45) Date of Patent: Sep. 26, 2023

(54) SYSTEMS AND METHODS FOR MANUFACTURING 3D PRINTED MEDICAL DEVICES

(71) Applicant: Medtronic, Inc., Minneapolis, MN (US)

(72) Inventors: Jonathan E. Baxter, Fridley, MN (US); Kristin M. Johnson, Circle Pines, MN (US); Gregory N. Nesseth, Forest Lake, MN (US); Jay T. Rassat, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/389,226

(22) Filed: Jul. 29, 2021

(65) Prior Publication Data
US 2022/0032002 A1     Feb. 3, 2022

Related U.S. Application Data

(60) Provisional application No. 63/059,867, filed on Jul. 31, 2020.

(51) Int. Cl.
*B33Y 10/00*     (2015.01)
*A61M 25/00*     (2006.01)
(Continued)

(52) U.S. Cl.
CPC ....... *A61M 25/0009* (2013.01); *B29C 64/118* (2017.08); *B29C 64/209* (2017.08);
(Continued)

(58) Field of Classification Search
CPC .......................... B29C 64/209; B29C 64/118
See application file for complete search history.

(56) References Cited

U.S. PATENT DOCUMENTS

| 2,764,148 A | 9/1956 | Sheldon |
| 3,485,234 A | 12/1969 | Stevens |
(Continued)

FOREIGN PATENT DOCUMENTS

| CA | 2998126 | 10/2018 |
| EP | 1053039 | 11/2000 |
(Continued)

OTHER PUBLICATIONS

International Search Report and Written Opinion prepared for International Application No. PCT/US2021/043794, dated Nov. 23, 2021. 11 pages.
(Continued)

*Primary Examiner* — Yung-Sheng M Tsui
*Assistant Examiner* — Melody Tsui
(74) *Attorney, Agent, or Firm* — Mueting Raasch Group

(57) ABSTRACT

Systems and methods for manufacturing an elongate medical device including various surface features. The system including a heating cartridge, a heating element, a filament handling system, a substrate handling system, a controller, and one or more additional components adapted to form the surface features on the medical device. The heating element melts a filament material within the heating cartridge to form a jacket of the medical device and the one or more additional components engages the outer surface of the jacket to create surface features.

12 Claims, 15 Drawing Sheets

(51) Int. Cl.
*B33Y 30/00* (2015.01)
*B33Y 40/00* (2020.01)
*B33Y 50/02* (2015.01)
*B33Y 80/00* (2015.01)
*B29C 64/118* (2017.01)
*B29C 64/295* (2017.01)
*B29C 64/209* (2017.01)
*B29C 64/393* (2017.01)
*B29C 64/336* (2017.01)
*B29L 31/00* (2006.01)

(52) U.S. Cl.
CPC .......... *B29C 64/295* (2017.08); *B29C 64/336* (2017.08); *B29C 64/393* (2017.08); *B33Y 10/00* (2014.12); *B33Y 30/00* (2014.12); *B33Y 40/00* (2014.12); *B33Y 50/02* (2014.12); *B33Y 80/00* (2014.12); *A61M 2207/10* (2013.01); *B29L 2031/7542* (2013.01)

(56) References Cited

U.S. PATENT DOCUMENTS

| | | | |
|---|---|---|---|
| 5,871,475 | A | 2/1999 | Frassica |
| 6,591,472 | B1 | 7/2003 | Noone et al. |
| 7,306,617 | B2 | 12/2007 | Majercak |
| 7,833,218 | B2 | 11/2010 | Lunn et al. |
| 7,909,033 | B2 | 3/2011 | Faram |
| 8,118,827 | B2 | 2/2012 | Duerig et al. |
| 8,509,916 | B2 | 8/2013 | Byrd et al. |
| 9,002,496 | B2 | 4/2015 | Elsey |
| 9,043,191 | B2 | 5/2015 | Grady et al. |
| 9,974,887 | B2 | 5/2018 | Eversull et al. |
| 10,254,499 | B1* | 4/2019 | Cohen ................ H01R 4/024 |
| 10,327,862 | B2 | 6/2019 | Lubinski |
| 10,442,175 | B2 | 10/2019 | Schlachter |
| 10,548,355 | B2 | 2/2020 | Volpis et al. |
| 10,610,666 | B2 | 4/2020 | Stern |
| 10,751,507 | B2 | 8/2020 | Palmer et al. |
| 2004/0002677 | A1 | 1/2004 | Gentsler |
| 2007/0005041 | A1 | 1/2007 | Frassica et al. |
| 2007/0060863 | A1 | 3/2007 | Goeken et al. |
| 2008/0262472 | A1 | 10/2008 | Lunn et al. |
| 2012/0149985 | A1 | 6/2012 | Frassica et al. |
| 2014/0284838 | A1 | 9/2014 | Pfeffer et al. |
| 2014/0361460 | A1* | 12/2014 | Mark ................ B33Y 50/02 264/248 |
| 2015/0217517 | A1 | 8/2015 | Karpas et al. |
| 2016/0096323 | A1 | 4/2016 | Fry et al. |
| 2016/0101262 | A1 | 4/2016 | Root et al. |
| 2016/0184233 | A1 | 6/2016 | Palomar-Moreno et al. |
| 2016/0207220 | A1 | 7/2016 | Hack et al. |
| 2016/0303347 | A1 | 10/2016 | Porter |
| 2017/0182290 | A1 | 6/2017 | Stern |
| 2017/0189553 | A1 | 7/2017 | Hunter |
| 2017/0259506 | A1 | 9/2017 | Ho et al. |
| 2018/0036123 | A1 | 2/2018 | Costello |
| 2018/0065320 | A1* | 3/2018 | Tyler ................ B29C 48/12 |
| 2018/0117855 | A1 | 5/2018 | Girou et al. |
| 2018/0141274 | A1 | 5/2018 | Fink et al. |
| 2018/0168687 | A1 | 6/2018 | Drake et al. |
| 2018/0254099 | A1 | 9/2018 | Beydoun et al. |
| 2018/0289925 | A1 | 10/2018 | Palmer et al. |
| 2018/0370117 | A1 | 12/2018 | Gardiner et al. |
| 2019/0002625 | A1 | 1/2019 | Jiang et al. |
| 2019/0240456 | A1 | 8/2019 | Pokorny et al. |
| 2019/0351185 | A1 | 11/2019 | Assouline et al. |
| 2019/0375149 | A1 | 12/2019 | Limem et al. |
| 2020/0080237 | A1 | 3/2020 | Vogt et al. |
| 2020/0093505 | A1 | 3/2020 | Sinelnikov et al. |
| 2021/0122115 | A1 | 4/2021 | Ramos |
| 2021/0236767 | A1 | 8/2021 | Warnock, Jr. et al. |
| 2021/0298730 | A1 | 9/2021 | Baxter et al. |
| 2022/0226636 | A1 | 1/2022 | Rassat et al. |
| 2022/0032003 | A1 | 2/2022 | Baxter et al. |
| 2022/0032537 | A1 | 2/2022 | Baxter et al. |

FOREIGN PATENT DOCUMENTS

| | | |
|---|---|---|
| KR | 101863192 | 6/2018 |
| WO | 2014/172545 | 10/2014 |
| WO | 2016/168505 | 10/2016 |
| WO | 2019/070899 | 4/2019 |

OTHER PUBLICATIONS

International Preliminary Report on Patentability for PCT Application No. PCT/US2021/024640 dated Oct. 13, 2022, 10 pages.
Ascend Medical Technologies, "Design Guidelines for 3D X-Fusion Technology", ascendmedtech.com/design-guidelines, retrieved Oct. 25, 2019, 3 pages.
Ascend Medical Technologies, "Engineering Capabilities", ascendmedtech.com/design-guidelines, retrieved Oct. 25, 2019, 7 pages.
Baxter et al., U.S. Appl. No. 17/215,842, filed Mar. 29, 2021.
Dilberoglu et al., "Current trends and research opportunities in hybrid additive manufacturing", The International Journal of Advanced Manufacturing Technology, 113, 2021, pp. 623-648.
Gardeski et al., U.S. Appl. No. 63/001,832, filed Mar. 30, 2020.
Gardeski et al., U.S. Appl. No. 17/215,842, filed Mar. 29, 2021.
Ramos et al., U.S. Appl. No. 62/927,092, filed Oct. 28, 2019.
Ramos et al., U.S. Appl. No. 17/081,815, filed Oct. 27, 2020.
Warnock Jr. et al., U.S. Appl. No. 62/970,561, filed Feb. 5, 2020.
Warnock Jr. et al., U.S. Appl. No. 17/162,101, filed Jan. 29, 2021.
International Search Report and Written Opinion from PCT Application No. PCT/US2021/024640 dated Sep. 13, 2021, 17 pages.
International Search Report and Written Opinion from PCT Application No. PCT/US2022/012966, dated Jun. 13, 2022, 19 pages.
International Search Report and Written Opinion from PCT/US2021/043795 dated Oct. 20, 2021, 14 pages.
International Search Report and Written Opinion from PCT/US2021/043914 dated Dec. 20, 2021, 18 pages.
International Preliminary Report on Patentability for PCT/US2021/043794 dated Feb. 9, 2023 (9 pages).

* cited by examiner

SYSTEMS AND METHODS FOR MANUFACTURING 3D PRINTED MEDICAL DEVICES

This application claims the benefit of U.S. Provisional Patent Application Ser. No. 63/059,867 filed on Jul. 31, 2020, which is incorporated by reference herein in its entirety.

The disclosure generally relates to medical devices and, in particular, additive manufacturing or 3D printing of medical devices, such as catheters and implantable stimulation leads.

Medical catheters and leads are commonly used to access vascular and other locations within a body and to perform various functions at those locations, for example, delivery catheters may be used to deliver medical devices, such as implantable medical leads. A number of such medical devices are designed to be navigated through tortuous paths in a human body, such as through a patient's vasculature. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls and the like. These contrasting properties can present challenges in designing and manufacturing catheters. Existing manufacturing processes, such as conventional extrusion, may also limit options in designing and manufacturing catheters.

SUMMARY

The techniques of the present disclosure generally relate to additive manufacturing of medical devices, such as catheters and leads, that allows for further customization of the medical devices. For example, the systems and techniques described herein may allow for integrating features quickly, iterating designs, and designing new geometries and features in a more specific manner. Specifically, the shape and/or size of the medical device or features disposed thereon may be readily manufactured to the operators specifications. Therefore, the unique characteristics of a patient's vasculature may be accounted for when designing and manufacturing the medical device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
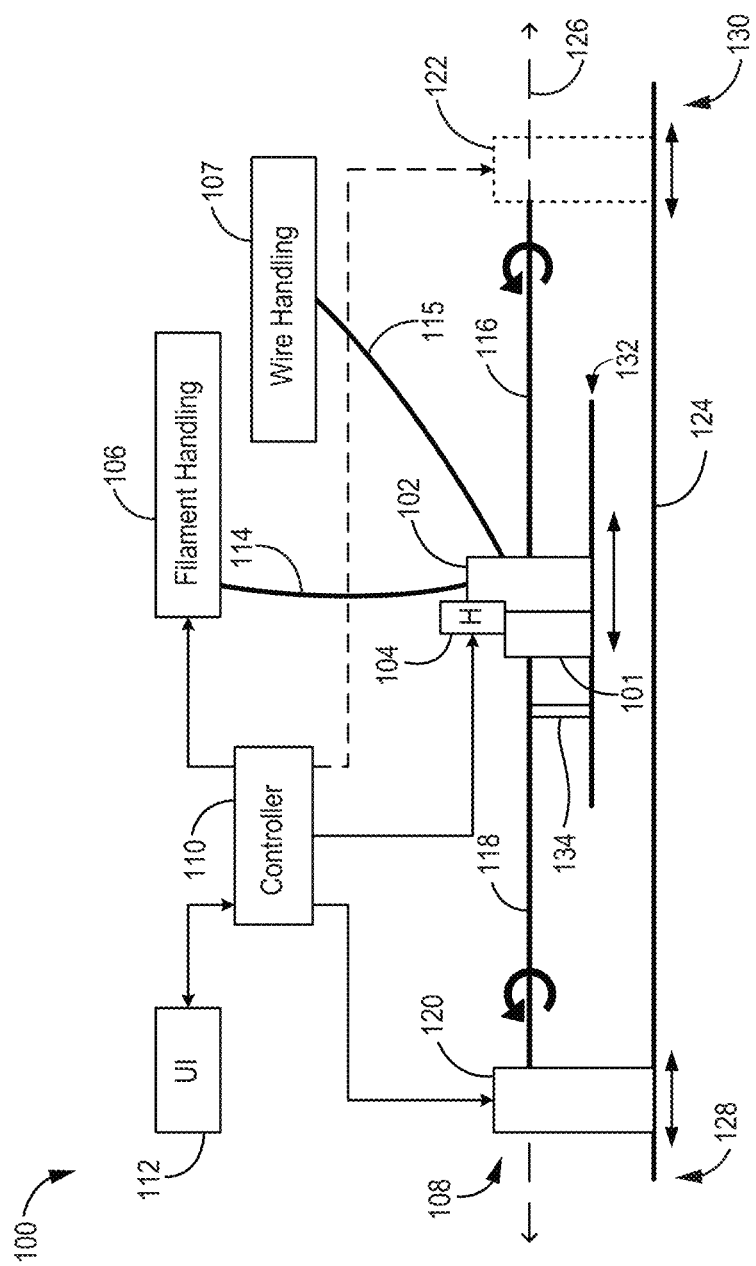
FIG. 1 is a conceptual diagram of an illustrative additive manufacturing system according to the present disclosure.

The present disclosure generally provides additive manufacturing systems and methods for medical devices, such as catheters and leads, that allows for customization of the medical device. Additive manufacturing may also be described as three-dimensional (3D) printing. By using an additive manufacturing process, a wider variety of hardness levels can be achieved compared to existing techniques to produce catheters, catheter components, or implantable devices. Further, the additive manufacturing process allows for various tooling and processes to design and develop specific medical device features (that may be difficult to otherwise make). For example, the system may operate similar to a polymer printer and polymer lathe to create and refine any particular medical device. As such, new designs and new dimensions may be created in an efficient way.

Specifically, designing the shape and dimensions of the medical device may be beneficial in customizing the medical device for a particular application. For example, a particular design/shape may be more specific to one patient as compared to another. Therefore, externally added three-dimensional surface protrusions (such as, e.g., threads, splines, nubs, or similar) may aid in the performance of the medical device by modifying the friction of interface surfaces between the medical device body and the anatomy of the patient. For example, in one or more embodiments, the surface features may provide anchoring mechanisms for screwing or threading the medical device into an annularity/cylindrical anatomical feature, or to create preferred performance characteristics (e.g., bending, straightening, torque, etc.). In other words, the medical device may be easily altered using the tooling and methods described herein to define further features of the medical device.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of an additive manufacturing system 100 according to the present disclosure. The system 100 may be configured and used to produce a catheter, catheter component, lead, or subassembly. The system 100 may use or include consumable filament materials or pellet form resins having a wide variety of hardness levels. The system 100 may be configured to operate a wide variety of process conditions to produce catheters, catheter components, leads, or subassemblies using filaments or pellet form resins of various hardness levels. In general, the system 100 defines a distal region 128, or distal end, and a proximal region 130, or proximal end. The system 100 may include a platform 124 including a rigid frame to support one or more components of the system.

Further components of the system 100 may be shown as described in U.S. Pat. App. No. 62/927,092, entitled "ADDITIVE MANUFACTUING FOR MEDICAL DEVICES," which is herein incorporated by reference. For example, as shown in the illustrated embodiment, the system 100 may include one or more components, such as a heating cartridge 102, a heating element 104, a filament handling system 106, an optional wire handling system 107, a substrate handling system 108, a controller 110, and a user interface 112. The filament handling system 106 may be operably coupled to the heating cartridge 102. The filament handling system 106 may provide one or more filaments 114 to the heating cartridge 102. The optional wire handling system 107 may be used to provide one or more wires 115 to the heating cartridge 102. The heating element 104 may be operably coupled, or thermally coupled, to the heating cartridge 102. The heating element 104 may provide heat to melt filament material in the heating cartridge 102 from the one or more filaments 114 provided by the filament handling system 106. The optional wires 115 may not be melted by the heating cartridge 102. The substrate handling system 108 may be operably coupled to the heating cartridge 102. The substrate handling system 108 may provide a substrate 116 that extends through the heating cartridge. Melted filament material located in the heating cartridge 102 may be applied to the substrate 116. The substrate 116 or the heating cartridge 102 may be translated or rotated relative to one another by the substrate handling system 108. The substrate handling system 108 may be used to move the substrate 116 or the heating cartridge 102 relative to one another to cover the substrate 116 with the melted filament material to form a jacket 118. The optional wires 115 may be incorporated into the jacket 118 (e.g., molded into, bedded within, etc.).

The substrate 116 may also be described as a mandrel or rod. The jacket 118 may be formed or deposited around the substrate 116. In some embodiments, the jacket 118 may be formed concentrically around the substrate 116. In one example, the jacket 118 is formed concentrically and centered around the substrate 116.

Figure 6:
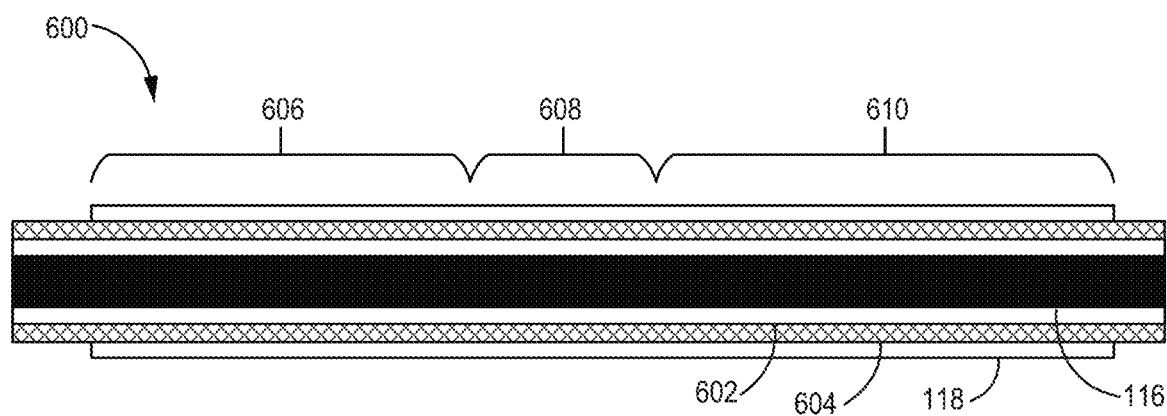
FIG. 6 is a conceptual diagram of an illustrative catheter that may be manufactured, before the substrate is removed, using the additive manufacturing system of FIG. 1.

When the system 100 is used to make a catheter or catheter component, the jacket 118 may be described as a catheter jacket. Some or all of the substrate 116 may be removed or separated from the jacket 118 and the remaining structure coupled to the jacket may form the catheter or catheter component, such as a sheath. One example of a catheter that may be formed by the system 100 is shown in FIG. 6.

The substrate 116 may be formed of any suitable material capable of allowing melted filament material to be formed thereon. In some embodiments, the substrate 116 is formed of a material that melts at a higher temperature than any of the filaments 114. One example of a material that may be used to form the substrate 116 includes stainless steel.

The controller 110 may be operably coupled to one or more of the heating element 104, the filament handling system 106, the substrate handling system 108, and the user interface 112. The controller 110 may activate, or initiate or otherwise "turn on," the heating element 104 to provide heat to the heating cartridge 102 to melt the filament material located therein. Further, the controller 110 may control or command one or more motors or actuators of various portions of the system 100. Furthermore, the controller 110 may control one or more motors or actuators the filament handling system 106 to provide one or more filaments 114. Further, the controller 110 may control one or more motors or actuators of the substrate handling system 108 to move one or both of the heating cartridge 102 or the substrate 116 relative to one another. Further still, the controller 110 may send or receive data to the user interface 112, for example, to display information or to receive user commands. Control of the components operably coupled to the controller 110 may be determined based on user commands received by the user interface 112. In some embodiments, the user commands may be provided in the form of a machine-readable code or coding language.

Any suitable implementation may be used to provide the substrate handling system 108. In some embodiments, the substrate handling system 108 may include one or more of a head stock 120, an optional tail stock 122, and one or more motors coupled to or included in the head stock or tail stock. One or both of the head stock 120 and the tail stock 122 may be coupled to the platform 124. A stock may be defined as a structure that holds or secures the substrate 116 during formation of the jacket 118. The head stock 120 is defined as the stock closest to the end of the substrate 116 where formation of the jacket 118 begins in the formation process. In the illustrated embodiment, the jacket 118 is shown proximal to the head stock 120 and distal to the heating cartridge 102.

When the substrate 116 is secured by one or both stocks 120, 122, the substrate is generally positioned to pass through a substrate channel defined by the heating cartridge 102. One or both stocks 120, 122 may include a clamp or other securing mechanism to selectively hold the substrate 116. Such a clamp may be operably coupled to a substrate motor. In some embodiments, the substrate motor may be used to control opening and closing of the clamp. In some embodiments, the substrate motor may be used to rotate the substrate 116 in a clockwise or counterclockwise direction about a longitudinal axis 126. A translation motor may be operably coupled between a stock 120, 122 and the platform 124. In some embodiments, the translation motor may be used to translate the stock 120, 122 in a longitudinal direction along the longitudinal axis 126. In some embodiments, the translation motor also may be used to translate the stock 120, 122 in a lateral direction different than the longitudinal axis 126. The lateral direction may be oriented substantially orthogonal, or perpendicular, to the longitudinal axis 126.

In some embodiments, the substrate handling system 108 may be configured to move the head stock 120 at least in a longitudinal direction (for example, parallel to the longitudinal axis 126) relative to the platform 124. The substrate 116 may be fed through the substrate channel of the heating cartridge 102 by movement of the head stock 120 relative to the platform 124. A distal portion of the substrate 116 may be clamped into the head stock 120. The head stock 120 may be positioned close to the heating cartridge 102 at the beginning of the jacket formation process. The head stock 120 may move distally away from the heating cartridge 102, for example in a direction parallel to the longitudinal axis 126. In other words, the head stock 120 may move toward the distal region 128 of the system 100 while pulling the secured substrate 116 through the heating cartridge 102. As the substrate 116 passes through the heating cartridge 102, melted filament material from the filament 114 may be formed or deposited onto the substrate 116 to form the jacket 118. The heating cartridge 102 may be stationary relative to the platform 124. In some embodiments, the tail stock 122 may be omitted.

In some embodiments, the substrate handling system 108 may be configured to move the heating cartridge 102 at least in a longitudinal direction (along the longitudinal axis 126) relative to the platform 124. The substrate 116 may be fed through the substrate channel of the heating cartridge 102. A distal portion of the substrate 116 may be clamped into the head stock 120. A proximal portion of the substrate 116 may be clamped into the tail stock 122. In one example, the heating cartridge 102 may be positioned relatively close to the head stock 120 at the beginning of the jacket formation process. The heating cartridge 102 may move proximally away from the head stock 120. The heating cartridge 102 may move toward the proximal region 130 of the system 100. As the heating cartridge 102 passes over the substrate 116, melted filament material may be deposited onto the substrate 116 to form a jacket. The head stock 120 and the tail stock 122 may be stationary relative to the platform 124. In another example, the heating cartridge 102 may start near the tail stock 122 and move toward the distal region 128.

One or more motors of the substrate handling system 108 may be used to rotate one or both of the substrate 116 and the heating cartridge 102 relative to one another. In some embodiments, only the substrate 116 may be rotated about the longitudinal axis 126. In some embodiments, only the heating cartridge 102 may be rotated about the longitudinal axis 126. In some embodiments, both the substrate 116 and the heating cartridge 102 may be rotated about the longitudinal axis 126.

The heating cartridge 102 may be part of a subassembly 132. The subassembly 132 may be coupled to the platform 124. In some embodiments, one or more motors of the substrate handling system 108 may be coupled between subassembly 132 and the platform 124 to translate or rotate the subassembly 132, including the heating cartridge 102, relative to the platform 124 or the substrate 116. In some embodiments, one or more motors of the substrate handling system 108 may be coupled between a frame of the subassembly 132 and the heating cartridge 102 to translate or rotate the heating cartridge relative to the platform 124.

In some embodiments, the substrate 116 may be rotated about the longitudinal axis 126 relative to the heating cartridge 102 to facilitate forming certain structures of the jacket. In one example, the substrate 116 may be rotated by one or both of the head stock 120 and the tail stock 122 of the substrate handling system 108. In another example, the heating cartridge 102 or subassembly 132 may be rotated by the substrate handling system 108.

The system 100 may include one or more concentricity guides 134. The concentricity guide 134 may facilitate adjustments to the concentricity of the jacket around the substrate 116 before or after the substrate passes through the heating cartridge 102. The concentricity guide 134 may be longitudinally spaced from the heating cartridge 102. In some embodiments, the spacing may be greater than or equal to 1, 2, 3, 4, or 5 cm. The spacing may be sufficient to allow the jacket 118 to cool down and no longer be deformable. In some embodiments, one or more concentricity guides 134 may be positioned distal to the heating cartridge 102 and to engage the jacket 118. In some embodiments, one or more concentricity guides 134 may be positioned proximal to the heating cartridge 102 to engage the substrate 116. The concentricity guide 134 may mitigate drooping of the substrate 116 and may mitigate susceptibility to eccentricity in the alignment of the stock 120, 122 and the heating cartridge 102.

Any suitable implementation may be used to provide the filament handling system 106. One or more filaments 114 may be loaded into the filament handling system 106. For example, filaments 114 may be provided in the form of wound coils. Filaments 114 may be fed to the heating cartridge 102 by the filament handling system 106. In some embodiments, the filament handling system 106 may include one, two, or more pinch rollers to engage the one or more filaments 114. In some embodiments, the filament handling system 106 may include one or more motors. The one or more motors may be coupled to the one or more pinch rollers to control rotation of the pinch rollers. The force exerted by the motors onto the pinch rollers and thus onto the one or more filaments 114 may be controlled by the controller 110.

In some embodiments, the filament handling system 106 may be configured to feed the filaments 114 including at least a first filament and a second filament. The jacket 118 may be formed from the material of one or both of the filaments 114. The filament handling system 106 may be capable of selectively feeding the first filament and the second filament. For example, one motor may feed the first filament and another motor may feed the second filament. Each of the motors may be independently controlled by the controller 110. Selective, or independent, control of the feeds may allow for the same or different feed forces to be applied to each of the filaments 114.

The filaments 114 may be made of any suitable material, such as polyethylene, PEBAX elastomer (commercially available from Arkema S. A. of Colombes, France), nylon 12, polyurethane, polyester, liquid silicone rubber (LSR), or PTFE.

The filaments 114 may have any suitable Shore durometer. In some embodiments, the filaments 114 may have, or define, a Shore durometer suitable for use in a catheter. In some embodiments, the filaments 114 have a Shore durometer of at least 25A and up to 90A. In some embodiments, the filaments 114 have a Shore durometer of at least 25D and up to 80D.

In some embodiments, the filament handling system 106 may provide a soft filament as one of the filaments 114. In some embodiments, a soft filament may have a Shore durometer less than or equal to 90A, 80A, 70A, 80D, 72D, 70D, 60D, 50D, 40D, or 35D.

In some embodiments, the filament handling system 106 may provide a hard filament and a soft filament having a Shore durometer less than the soft filament. In some embodiments, the soft filament has a Shore durometer that is 10D, 20D, 30D, 35D, or 40D less than a Shore durometer of the hard filament.

The system 100 may be configured to provide a jacket 118 between the Shore durometers of a hard filament and a soft filament. In some embodiments, the filament handling system 106 may provide a hard filament having a Shore durometer equal to 72D and a soft filament having a Shore durometer equal to 35D. The system 100 may be capable of providing a jacket 118 having a Shore durometer that is equal to or greater than 35D and less than or equal to 72D.

The system 100 may be configured to provide a jacket 118 having, or defining, segments with different Shore durometers. In some embodiments, the system 100 may be capable of providing a jacket 118 having one or more of a 35D segment, a 40D segment, 55D segment, and a 72D segment.

The filaments 114 may have any suitable width or diameter. In some embodiments, the filaments 114 have a width or diameter of 1.75 mm. In some embodiments, the filaments 114 have a width or diameter of less than or equal to 1.75, 1.5, 1.25, 1, 0.75, or 0.5 mm.

Segments may have uniform or non-uniform Shore durometers. The system 100 may be configured to provide jacket 118 having one or more segments with non-uniform Shore durometers. In some embodiments, the jacket 118 may include continuous transitions between at least two different Shore durometers, for example, as shown in FIG. 6.

The controller 110 may be configured to change a feeding force applied to one or more of the filaments 114 to change a ratio of material in the jacket over a longitudinal distance. By varying the feeding force, the system 100 may provide different Shore durometer segments in a jacket 118, whether uniform or non-uniform. In one example, sharp transitions between uniform segments may be provided by stopping or slowing longitudinal movement while continuously, or discretely with a large step, changing the feeding force of one filament relative to another filament of the substrate 116 relative to the heating cartridge 102. In another example, gradual transitions between segments may be provided by continuously, or discretely with small steps, changing the feeding force of one filament relative to another filament while longitudinally moving the substrate 116 relative to the heating cartridge 102.

The one or more wires 115 provided by the wire handling system 107 may be introduced in any suitable manner. In some embodiments, the wires 115 may be attached to the substrate 116 and pulled by movement of the substrate. One example of a wire is a pull wire that may be used to steer the catheter produced by the system 100. In some embodiments, a particularly shaped heating cartridge may be used to accommodate one or more wires 115.

Any suitable type of heating element 104 may be used. In some embodiments, the heating element 104 may be a resistive-type heating element, which may provide heat in response to an electrical current. Other types of heating elements that may be used for the heating element 104 include a radio frequency (RF) or ultrasonic-type heating element. The heating element 104 may be capable of providing heat sufficient to melt the filaments 114. In some embodiments, the heating element 104 may heat the filaments 114 to greater than or equal to 235, 240, 250, or 260 degrees Celsius. In general, the one or more heating elements 104 may be used to heat the filaments 114 to any suitable melting temperature known to one of ordinary skill in the art having the benefit of this disclosure.

Figure 2:
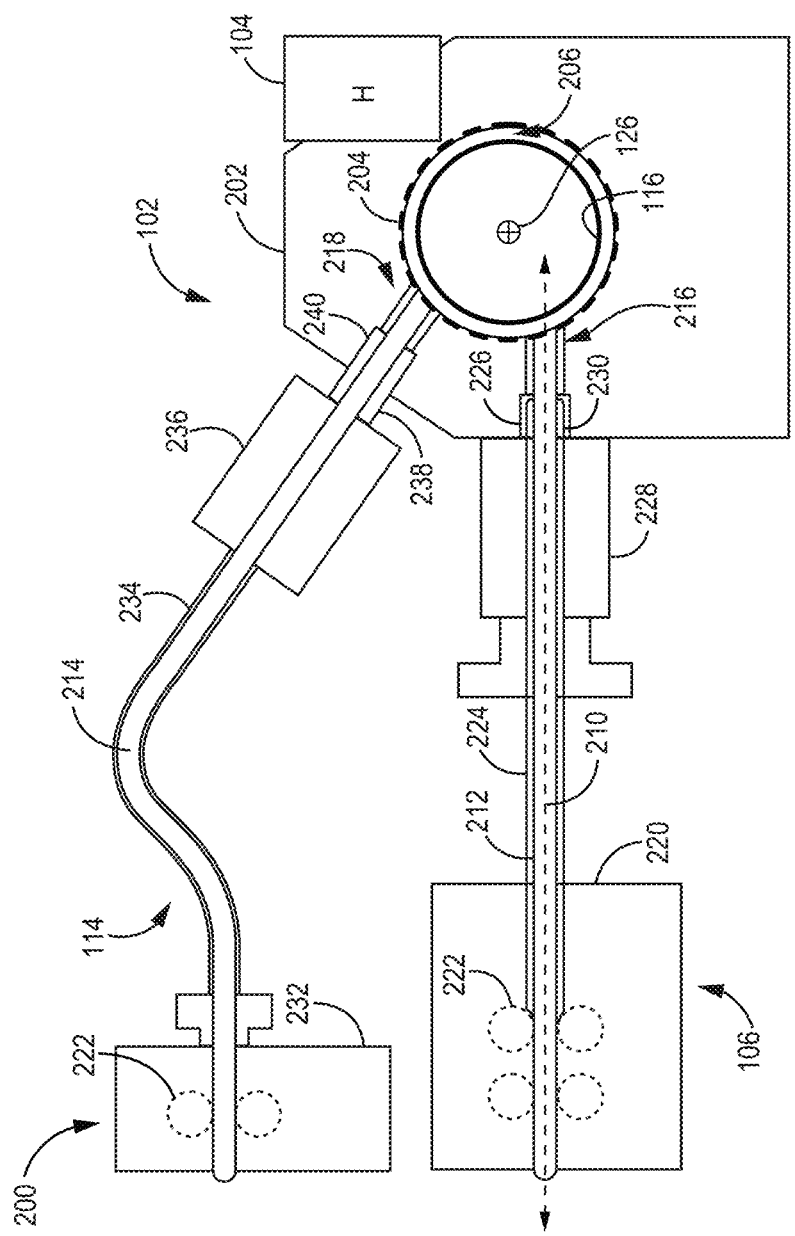
FIG. 2 is a conceptual diagram of an illustrative additive manufacturing apparatus for use with, for example, the additive manufacturing system of FIG. 1.

FIG. 2 shows one example of an additive manufacturing apparatus 200 of the additive manufacturing system 100 in an end view along the longitudinal axis 126, which is illustrated as a circle and cross. More detail of some components of the additive manufacturing system 100 are shown, such as the heating cartridge 102 and the filament handling system 106.

The heating cartridge 102 may include a heating block 202 at least partially defining an interior volume 204. The interior volume 204 may be heated by the heating element 104. The heating element 104 may be thermally coupled to the heating block 202 to melt filament material in the interior volume 204. In general, the system 100 may be configured to melt any portion of the filaments 114 in the interior volume 204. The heating element 104 may be disposed in an exposed or exterior volume defined in the heating block 202. The heating element 104 may be positioned proximate to or adjacent to the interior volume 204. In some embodiments, one, two, three, or more heating elements 104 may be thermally coupled to the heating block 202.

The heating block 202 may allow the substrate 116, which may be an elongate substrate or member, to pass through the heating block. The substrate 116 may be able to extend, or pass, through the interior volume 204. The substrate channel 206 defined by the heating cartridge 102 may extend through the interior volume 204. The substrate channel 206 may extend in a same or similar direction as the substrate 116. The substrate channel 206 may extend along the longitudinal axis 126.

A width or diameter of the interior volume 204 is larger than a width or diameter of the substrate 116. The width or diameter of the interior volume 204 or the substrate 116 is defined in a lateral direction, which may be orthogonal to the longitudinal axis 126. In one example, the lateral direction may be defined along a lateral axis 210. In some embodiments, the clearance between the substrate 116 and interior volume 204 is relatively small to facilitate changes in composition of filament material used to form the jacket 118 (FIG. 1) around the substrate 116.

The portion of the interior volume 204 around the substrate 116 may receive a flow of melted filament material from the filaments 114. When more than one filament material is provided to the interior volume 204, the filament materials may flow and blend, or mix, around the substrate 116.

In the illustrated embodiment, the filaments 114 includes a first filament 212 and a second filament 214. The first filament 212 may be provided into the interior volume 204 through a first filament port 216 at least partially defined by the heating block 202. The second filament 214 may be provided into the interior volume 204 through a second filament port 218 at least partially defined by the heating block 202. Each filament port 216, 218 may be at least partially defined by the heating block 202. Each filament port 216, 218 may be in fluid communication with the interior volume 204.

The filaments 114 may be delivered to the interior volume 204 in the same or different manners. In the illustrated embodiment, the first filament 212 is delivered to the interior volume 204 in a different manner than the second filament 214.

The filament handling system 106 may include a first handling subassembly 220. The first handling subassembly 220 may deliver the first filament 212 to the interior volume 204. The first handling subassembly 220 may include one or more pinch rollers 222. Each of the one or more pinch rollers 222 may be operably coupled to a motor. Any suitable number of pinch rollers 222 may be used. As illustrated, the first handling subassembly 220 may include two sets of pinch rollers 222. Pinch rollers 222 may be used to apply a motive force to the first filament 212 to move the first filament, for example, toward the interior volume 204.

The heating cartridge 102 may include a first guide sheath 224. The first guide sheath 224 may extend between the filament handling system 106 and the interior volume 204. The first guide sheath 224 may be coupled to the heating block 202. The first guide sheath 224 may extend into the first filament port 216 from an exterior of the heating block 202. The first guide sheath 224 may define a lumen in fluid communication with the interior volume 204. An inner width or diameter of the lumen may be defined to be greater than a width or diameter of the first filament 212. The first filament 212 may extend through the first guide sheath 224 from the pinch rollers 222 of the first handling subassembly 220 to the first filament port 216 and extend distally past the first guide sheath 224 into the interior volume 204.

As used herein with respect to the filaments 114, the term "distal" refers to a direction closer to the interior volume 204 and the term "proximal" refers to a direction closer to the filament handling system 106.

In some embodiments, a proximal end of the first guide sheath 224 may terminate proximate to one of the pinch rollers 222. A distal end of the first guide sheath 224 may terminate at a shoulder 226 defined by the first filament port 216. A distal portion or distal end of the first guide sheath 224 may be positioned proximate to or adjacent to the interior volume 204.

The inner width or diameter of the lumen of the first guide sheath 224 may be defined to be substantially the same or equal to an inner width or diameter of the first filament port 216, such as a smallest inner width or diameter of the first filament port. In other words, an inner surface of the first guide sheath 224 may be flush with an inner surface of the first filament port 216.

In some embodiments, the heating cartridge 102 may include a support element 228. The support element 228 may be coupled to the first guide sheath 224. The first guide sheath 224 may extend through a lumen defined by the support element 228. The support element 228 may be proximate to the heating block 202. In the illustrated embodiment, the support element 228 is coupled to the heating block 202. The support element 228 may include a coupling protrusion configured to be mechanically coupled to a coupling receptacle 230 defined by the first filament port 216. In some embodiments, the coupling receptacle 230 may define threads and the coupling protrusion of the support element 228 may define complementary threads.

The coupling receptacle 230 may terminate at the shoulder 226 of the first filament port 216. The coupling protrusion of the support element 228 may be designed to terminate at the shoulder 226. In some embodiments, a distal end of the support element 228 and the distal end of the first guide sheath 224 may engage the shoulder 226. In other embodiments, the distal end of the support element 228 may engage the shoulder 226 and the distal end of the first guide sheath 224 may engage a second shoulder (not shown) defined by the first filament port 216 distal to the shoulder 226.

When the first filament port 216 defines one shoulder, the first filament port 216 may define at least two different inner widths or diameters. The larger inner width or diameter may be sized to thread the support element 228 and the smaller inner width or diameter may be sized to match the inner width or diameter of the first guide sheath 224.

When the second filament port 218 defines two shoulders, the first filament port 216 may define at least three different inner widths or diameters. The largest inner width or diameter may be sized to thread the support element 228. The intermediate inner width or diameter may be sized to receive a distal portion of the first guide sheath 224. The smallest inner width or diameter may be sized to match the inner width or diameter of the first guide sheath 224.

The filament handling system 106 may include a second handling subassembly 232. The second handling subassembly 232 may deliver the second filament 214 to the interior volume 204. The second handling subassembly 232 may include one or more pinch rollers 222. Each of the one or more pinch rollers 222 may be operably coupled to a motor. Any suitable number of pinch rollers 222 may be used. As illustrated, the second handling subassembly 232 may include one set of pinch rollers 222. Pinch rollers 222 may be used to apply a motive force to the second filament 214.

The heating cartridge 102 may include one or more of a second guide sheath 234, a heat sink 236, and a heat break 238. The second guide sheath 234 may extend at least between the second handling subassembly 232 and the heat sink 236. The second guide sheath 234 may be coupled to the heat sink. The second guide sheath 234 may be coupled to the second handling subassembly 232. The heat sink 236 may be coupled to the heat break 238. The heat break 238 may be coupled to the heat block 202. The heat break 238 may extend into the second filament port 218 from an exterior of the heating block 202.

The second guide sheath 234 may define a lumen in fluid communication with the interior volume 204. The second filament 214 may extend through the second guide sheath 234 from the second handling subassembly 232 to the heat sink 236, through the heat sink 236, through the heat break, and through the second filament port 218. In some embodiments, the second guide sheath 234 may extend to the pinch rollers 22 in the second handling subassembly 232. In some embodiments, the second guide sheath 234 may extend at least partially into the heat sink 236.

The heat break 238 may be proximate to the heating block 202. The heat break 238 may be positioned between the heat sink 236 and the heating block 202. The heat break 238 may include a coupling protrusion configured to mechanically couple to a coupling receptacle 240 defined by the second filament port 218. In some embodiments, the coupling receptacle 240 may define threads and the coupling protrusion of the heat break 238 may define complementary threads. The second filament port 218 may include one or more shoulders such as those described with respect to the first filament port 216, except that the second filament port 218 may not be configured to receive the second guide sheath 234. The inner width or diameter of the support element 228 may be larger than the inner width or diameter of the heat break 238, for example, to accommodate the outer width or diameter of the first guide sheath 224. In other embodiments, the second filament port 218 may be configured to receive the second guide sheath 234 in a similar manner to the first filament port 216 receiving the first guide sheath 224.

Any suitable material may be used to make the guide sheaths 224, 234. In some embodiments, one or both guide sheaths 224, 234 may include a synthetic fluoropolymer. One or both guide sheaths 224, 234 may include polytetrafluoroethylene (PTFE). Another suitable material may include an ultra-high molecular weight polyethylene (UHMWPE).

Any suitable material may be used to make the support element 228. In some embodiments, the support element 228 may be a thermal insulator. The support element 228 may include a thermoplastic. The support element 228 may be made of a polyamide-imide, such as a TORLON polyamide-imide (commercially available from McMaster-Carr Supply Co. of Elmhurst, Ill.). Other suitable materials may include liquid-crystal polymer, polyaryletherketone (PAEK), polyphenylene sulfide, and polysulfone.

The support element 228 may provide mechanical support to the first guide sheath 224. The support element 228 may include a substantially rigid material. In some embodiments, the support element 228 include a material having a higher durometer than material used to make the first guide sheath 224.

Any suitable material may be used to make the heat sink 236. The heat sink 236 may include a high thermal conductivity material. In some embodiments, the heat sink 236 includes aluminum.

Any suitable material may be used to make the heat break 238. The heat break 238 may include a low thermal conductivity material. In some embodiments, the heat break 238 includes titanium. The heat break 238 may include a necked portion to reduce the amount of material between a proximal portion and a distal portion of the heat break. The necked portion may facilitate a reduced thermal conductivity between the proximal portion and the distal portion of the heat break 238.

In general, use of the apparatus 200 may facilitate using softer filaments at high feed forces and pressures, which tend to compress the soft filament and may result in jamming. Using higher feed forces and pressures may allow for a greater range of process conditions and may provide a consistent jacket around the substrate. In particular, use of the first guide sheath 224 extending at least partially into the first filament port 216 may facilitate the use of softer filament and greater "push-ability." Additionally, or alternatively, the use of the support element 228 may also facilitate the use of softer filament and greater "push-ability." In other embodiments, the apparatus 200 may include a screw or static mixer to help push a softer filament. In other words, the screw or static mixer may provide a cavity for softer filament material to be moved forward between the threads of the screw.

Figure 3:
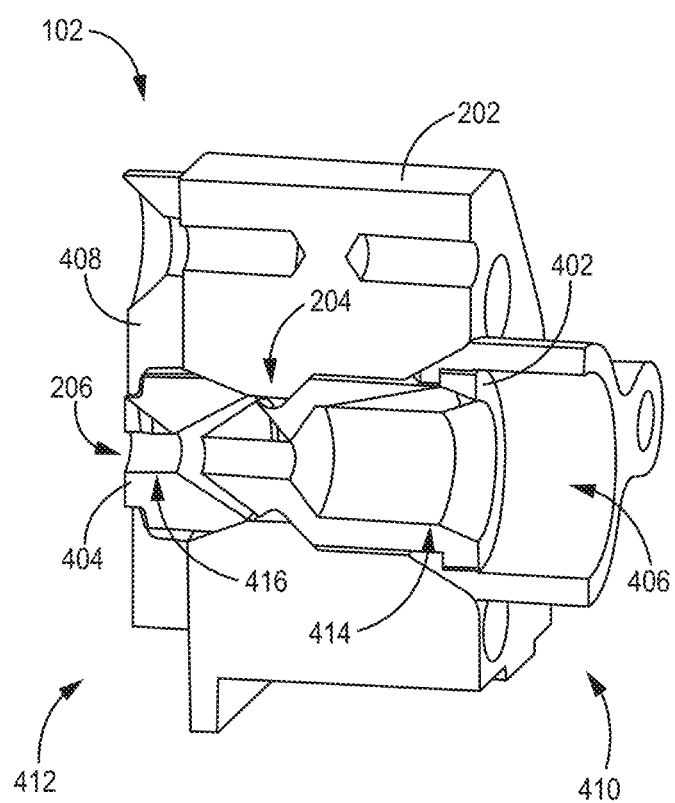
FIG. 3 is a conceptual diagram of an illustrative heating cartridge for use with, for example, the additive manufacturing system of FIG. 1.

FIG. 3 shows a partial cross-sectional side view of one example of the heating cartridge 102. The heating cartridge 102 or the heating block 202 may extend from a proximal side 410 to a distal side 412. In some embodiments, the heating cartridge 102 may include one or more of the heating block 202, an inlet die 402 coupled to the proximal side 410 of the heating block, an outlet die 404 coupled to the distal side 412 of the heating block, a proximal retaining plate 406 to facilitate retaining the inlet die adjacent to the heating block, and a distal retaining plate 408 to facilitate retaining the outlet die adjacent to the heating block.

The inlet die 402 and the outlet die 404 may be retained in any suitable manner. In the illustrated embodiment, the outlet die 404 may be retained by a distal shoulder of the distal retaining plate 408. In some embodiments, the inlet die 402 may be retained by the proximal retaining plate 406 between a distal shoulder of the proximal retaining plate 406 and a fastener, such as a nut with a lumen extending through, which may be threaded to the retaining plate to engage a proximal surface of the inlet die. The retaining plates 406, 408 may be fastened to the heating block 202 in any suitable manner.

The inlet die 402 may at least partially define a substrate inlet port 414. The outlet die 404 may at least partially define a substrate outlet port 416. The inlet die 402 may at least partially define the interior volume 204. The outlet die 404 may at least partially define the interior volume 204. In some embodiments, an exterior surface of the inlet die 402, an interior surface of the outlet die 404, and an interior surface of the heating block 202 may cooperatively define the interior volume 204.

The substrate channel 206 may be described as extending from the proximal side 410 to the distal side 412 of the heating cartridge 102, or vice versa. The substrate channel 206 may extend through the interior volume 204. As shown, the substrate channel 206 may extend through one or more of the proximal retaining plate 406, the inlet die 402, the heating block 202, the outlet die 404, and the distal retaining plate 408.

Figure 4:
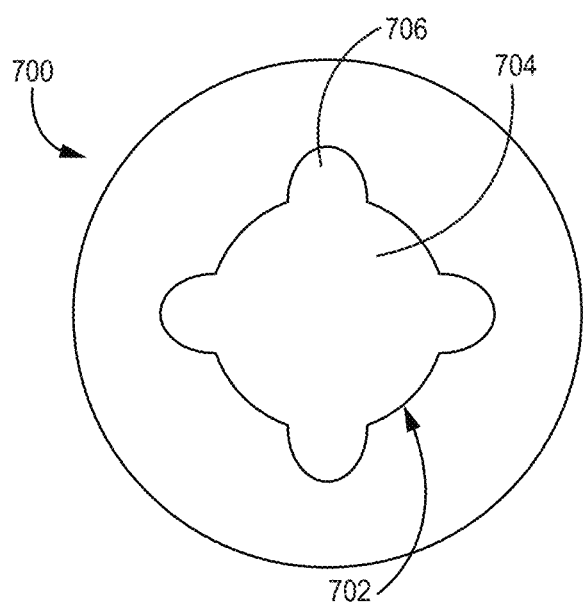
FIG. 4 is a conceptual diagram of an illustrative outlet die that may be used, for example, in the heating cartridge in the additive manufacturing system of FIG. 1.

FIG. 4 shows an end view of one example of an inlet or outlet die 700 that may be used in the heating cartridge 102 (FIG. 1). The die 700 may define a substrate inlet or outlet port 702. The port 702 may define a main region 704 and one, two, three, four, or more cutouts 706, or cutout regions. In the illustrated embodiment, the port 702 defines four cutouts 706.

When the interior cross-sectional shape die 700 is used in an outlet die, the jacket formed by the heating cartridge 102 may include a number of protrusions corresponding to the number of cutouts 706 used in the die 700. For example, the illustrated die 700 would produce four protrusions on the jacket.

In some embodiments, one or more of the cutouts 706 may be sized to receive a wire 115 (FIG. 1), such as a pull wire, which may be provided by the wire handling system 107 (FIG. 1). In some embodiments, the interior cross-sectional shape of die 700 may be used in both the input die and the outlet die to accommodate the wires 115 pulled through the cutouts 706.

Figure 5:
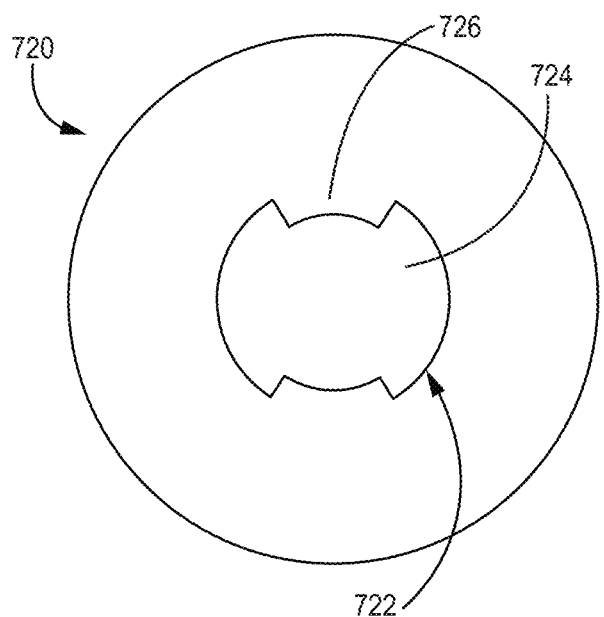
FIG. 5 is a conceptual diagram of another illustrative outlet die that may be used, for example, in the heating cartridge in the additive manufacturing system of FIG. 1.

FIG. 5 shows an end view one example of an inlet or outlet die 720 that may be used in the heating cartridge 102 (FIG. 1). The die 720 may define a substrate inlet or outlet port 722. The port 722 may define a main region 724 and one, two, three, four, or more protrusions 726, or cutout regions. In the illustrated embodiment, the port 722 defines two protrusions 726, or teeth.

When the interior cross-sectional shape die 720 is used in an outlet die, the jacket formed by the heating cartridge 102 may include a number of channels corresponding to the number of protrusions 726 used in the die 720. For example, the illustrated die 720 would produce two channels on the jacket.

FIG. 6 shows one example of a catheter 600 that may be manufactured using the system 100 before the substrate 116 is removed. The substrate 116 may include a lubricious coating on its exterior surface to facilitate removal. The lubricious coating may extend around the circumference of the substrate 116. One example of a lubricious coating is a PTFE coating.

The substrate 116 may be covered with a liner 602, such as a PTFE layer. The liner 602 may be placed over the lubricious coating. The liner 602 may extend around the circumference of the substrate 116.

The liner 602 may be covered with a braid 604, such as a stainless-steel braid layer. The braid 604 may be placed over the liner 602. The braid 604 may extend around the circumference of the liner 602. The braid 604 may be porous.

The jacket 118 may be applied to the braid 604. When the jacket 118 is formed, the liner 602 may adhere to the jacket 118 through pores in the braid 604.

In the illustrated embodiments, the catheter 600 includes a first segment 606, a second segment 608, and a third segment 610. Each segment 606, 608, 610 may have different durometers. In some embodiments, the first segment 606 may have a high durometer, the third segment 610 may have a low durometer, and the second segment 608 may have a continuously varying durometer in a longitudinal direction between the durometers of the first and third segments. For example, the first segment 606 may have a Shore durometer equal to 72D, the third segment 610 may have a Shore durometer equal to 35D, and the second segment 608 may have a Shore durometer that gradually changes from 72D to 35D over its length.

The jacket 118 produced by the system 100 may be altered and modified in a variety of different ways to provide specific features of the jacket 118. For example, as shown in FIG. 1, the system 100 may include an additional component 101 that operates to further process the jacket 118 to include various features. In one or more embodiments, the additional component 101 may be directly coupled to the heating cartridge 102. In other embodiments, the additional component 101 may be spaced apart from the heating cartridge 102 along the longitudinal axis 126. Whether the additional component 101 is directly attached or spaced apart from the heating cartridge 102, the additional component 101 may be positioned distal to (e.g., trailing) the heating cartridge 102 such that the additional component 101 may alter or modify the jacket 118 after it is formed by the heating cartridge 102.

Figure 7:
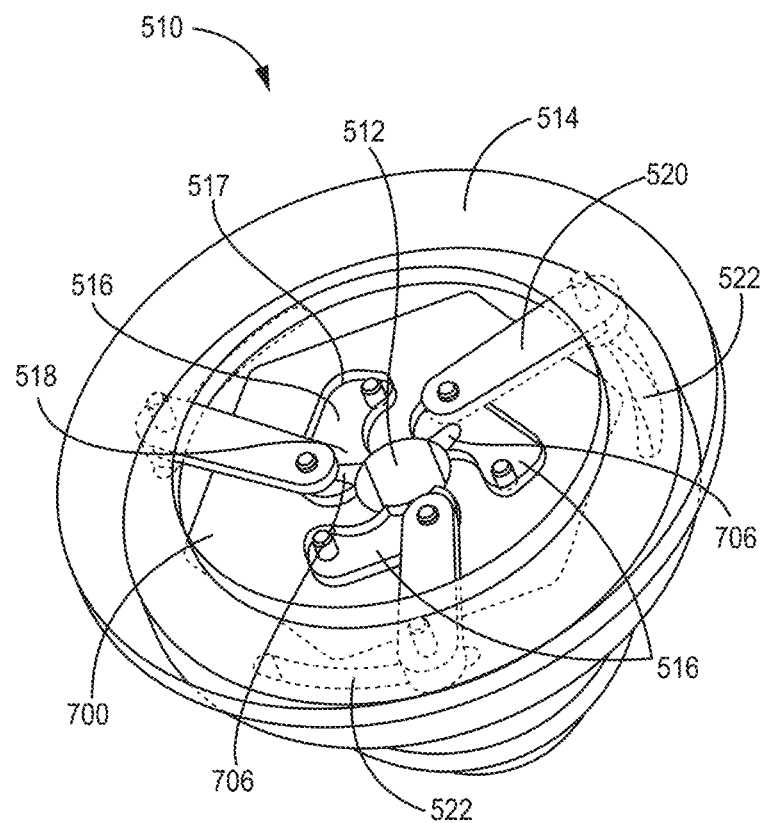
FIG. 7 is an image of an illustrative shutter for use with, for example, the additive manufacturing system of FIG. 1.

In one or embodiments, the system 100 may be adapted to selectively adjust the substrate outlet to modify the size and/or shape of the substrate outlet. In other words, the substrate outlet may be blocked or obstructed to further refine the shape of the material defining the jacket 118. Specifically, as shown in FIG. 7, the system 100 may include a shutter 510 that defines an opening 512 that coincides with and is spaced longitudinally from the substrate outlet. The shutter 510 may include a body portion 514 and one or more fins 516 movably coupled to the body portion 514 such that the one or more fins 516 are adapted to move relative to the substrate outlet to modify the size and/or shape of the substrate outlet. For example, the one or more fins 516 may modify the opening such that the profile of the jacket 118 extending through the substrate outlet may be consequently altered. The shutter 510 as described herein may operate similar to a camera shutter or iris.

The shutter 510 may be configured to modify the jacket 118 in various different ways. For example, the shutter 510 may expand and retract to alter the thickness or cross-sectional diameter of the jacket 118. Also, as shown in FIG. 7, the one or more fins 516 of the shutter 510 may alter or modify cutouts 706 of the outlet die 700 such that the one or more fins 516 may modify the size and/or shape of the cutouts 706 (and, therefore, may alter the characteristics of the resultant protrusions on the jacket 118). For example, the one or more fins 516 may be moved to alter the height of the cutouts 706 or remove the cutouts 706 altogether. In other words, the shutter 510 may be configured to toggle between creating a jacket with protrusions (e.g., when the fins are not blocking all or a portion of the cutouts) and a jacket without protrusions (e.g., when the fins are completely blocking the cutouts). Additionally, the shutter 510 may be configured to reduce the overall diameter of the outlet such that the resultant diameter of the jacket may be modified. Therefore, a varying output geometry (e.g., a tapered portion) may be defined on the jacket (e.g., proximate an end of the jacket) using the shutter 510.

Each of the one or more fins 516 may extend between a first end region 517 movably coupled to the body portion 514 (e.g., pivotable via a pin) and a second end region 518 adapted to move relative to the substrate outlet. In other words, the second end region 518 of the fin 516 may be adapted to cover up or block (e.g., at least a portion) of the substrate outlet (e.g., to define features of the jacket). Further, the shutter 510 may include one or more linkages 520, each linkage 520 corresponding to a fin of the one or more fins 516. Each linkage 520 may extend between a first end region movably coupled to the body portion and a second end region movably coupled to the corresponding fin 516 (e.g., pivotable via a pin). In one or more embodiments, the body portion 514 may define one or more slots 522 within which each linkage 520 (e.g., the first end region) is movably coupled.

Further, the controller may be adapted to change these characteristics along the length of the jacket by changing the positions of the one or more fins 516. In other words, the shutter 510 may be controllable to selectively position the one or more fins 516 relative to the substrate outlet and, thereby, affect the shape and/or size of the jacket. Therefore, when manufacturing the jacket, a user may specifically vary features of the jacket by controlling the shutter 510. In other words, the shutter 510 may be able to turn features on and off at specific times and locations in the printing of the jacket. Further, the one or more fins 516 of the shutter 510 can change the shape of the opening to provide radial tapering or embed a shape into the jacket.

The shutter 510 may be positioned relative to the heating cartridge (e.g., the substrate outlet port) in any suitable way. For example, in one or more embodiments, the shutter 510 may be located distal to the substrate outlet port. In other embodiments, the shutter 510 may be located proximal to the substrate outlet port (e.g., between the outlet die and the inlet die). Additionally, in one or more embodiments, the shutter 510 may be directly attached to the heat cartridge (e.g., to the outlet die). In other embodiments, the shutter 510 may be spaced apart from the heating cartridge. In such embodiments, the shutter 510 may move along with the heating cartridge to post-process the jacket after the jacket is formed.

Figure 8:
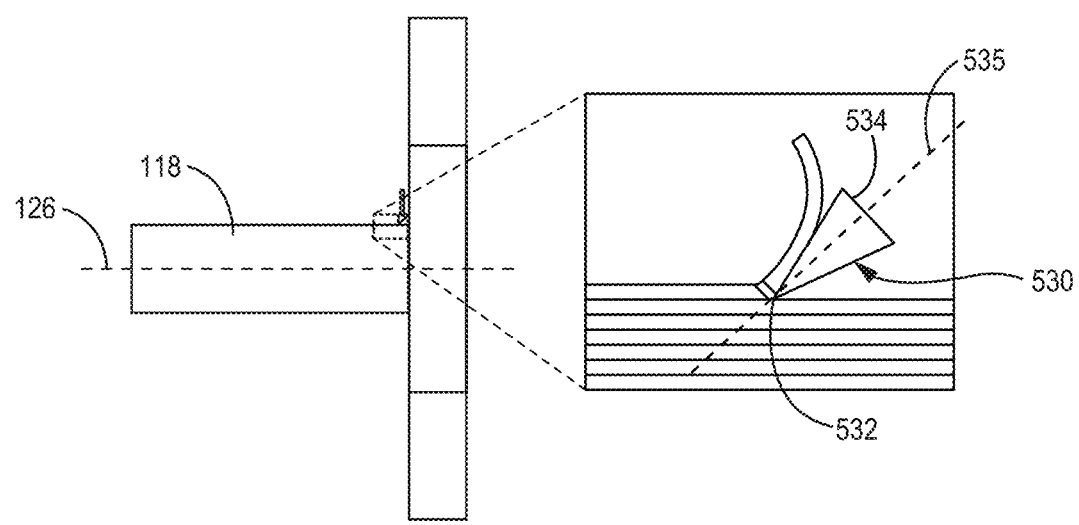
FIG. 8 is an image of an illustrative cutting tool for use with, for example, the additive manufacturing system of FIG. 1.

As shown in FIG. 8, the system 100 may include one or more cutting tools 530 to engage the jacket 118 and define features therein. For example, the cutting tools 530 may act as a surface modification tool to slice and/or raise the surface of the jacket 118 into various shapes (e.g., similar to a lathe or CNC type tool that could be called and move as needed). In one or more embodiments, the one or more cutting tools 530 may be heated to melt/soften and form a portion of the jacket 118 with which the cutting tool engages. Each cutting tool of the one or more cutting tools 530 may include a cutting edge 532 oriented towards the longitudinal axis 126 and may be configured to selectively engage the jacket 118. In other words, the cutting edge 532 of the cutting tool 530 may interact with the jacket 530 to remove material therefrom to define features on the surface of the jacket 118. For example, the features defined in the surface of the jacket 118 may be used to create structures that may interface with specific geometries and anatomical features of the vascular or to provide spaces/channels for various components to be placed therein.

The cutting edge 532 of the one or more cutting tools 530 may be positioned between an edge of the substrate outlet and the longitudinal axis so as to position the cutting edge 532 proximate an outer surface of the jacket 118 (e.g., being formed through the substrate outlet). For example, the cutting edge 532 of the one or more cutting tools 530 may be configured to engage the jacket 118 from a shallow cut that may act as a surface finish, a deep cut that extends the full depth/thickness of the jacket 118, or anywhere therebetween.

Each cutting tool of the one or more cutting tools 530 may extend between a base edge 534 and the cutting edge 532 along a cutting axis 535. In one or more embodiments, the cutting axis 535 may be positioned at a downward angle relative to the longitudinal axis 126 between about 0 and 180 degrees. Preferably, the cutting axis 535 may be positioned at a downward angle relative to the longitudinal axis of less than or equal to about 90 degrees, less than or equal to 75 degrees, less than or equal to 60 degrees, less than or equal to 45 degrees, etc. and/or greater than or equal to 0 degrees, greater than or equal to 15 degrees, greater than or equal to 30 degrees, greater than or equal to 40 degrees, etc.

Further, in one or more embodiments, the one or more cutting tools 530 may be movably coupled to the heating cartridge (e.g., at the base edge) or any other structure distal to the heating cartridge. As such, the one or more cutting tools 530 may be movable between an engaged position and a spaced apart position (e.g., pivoting between the positions). The cutting tool 530 (e.g., the cutting edge) may be in contact with the jacket 118 (e.g., so as to cut and define a portion of the jacket) when in the engaged position and not in contact with the jacket 118 when in the spaced apart position. In one or more embodiments, the movement may occur through pivoting the cutting tool 530 or moving the cutting tool 530 laterally into position. Further, in one or more embodiments, the one or more cutting tools 530 may be configured to move radially along the jacket 118 to a specific position.

The one or more cutting tools 530 may include any number of suitable cutting tools. For example, the one or more cutting tools 530 may include one, two, three, or four or more cutting tools. In one or more embodiments, the multiple cutting tools 530 may be configured to move independently from one another. It is noted that the controller may be configured to control the various movements of the one or more cutting tools 530.

The one or more cutting tools 530 may be positioned relative to the heating cartridge (e.g., the substrate outlet port) in any suitable way. For example, in one or more embodiments, the one or more cutting tools 530 may be located distal to the substrate outlet port. In other embodiments, the one or more cutting tools 530 may be located proximal to the substrate outlet port (e.g., between the outlet die and the inlet die). Additionally, in one or more embodiments, the one or more cutting tools 530 may be directly attached to the heat cartridge (e.g., to the outlet die). In other embodiments, the one or more cutting tools 530 may be spaced apart from the heating cartridge. In such embodiments, the one or more cutting tools 530 may move along with the heating cartridge to post-process the jacket after the jacket is formed.

Figure 9:
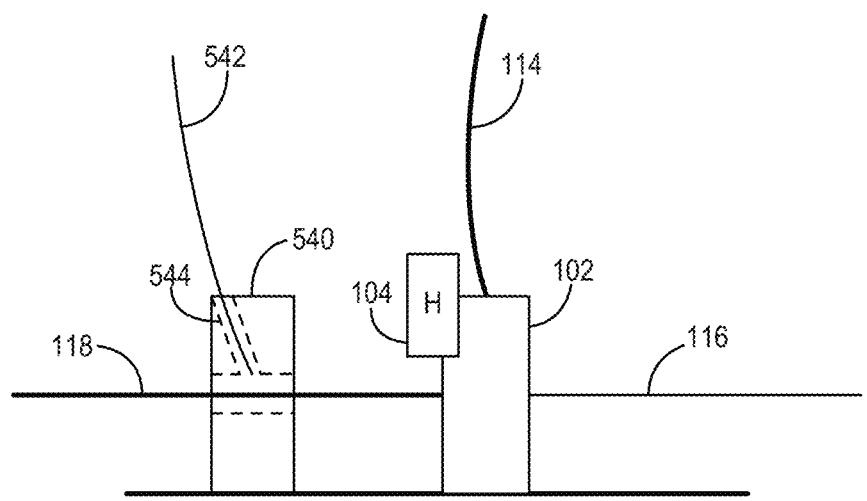
FIG. 9 is an image of an illustrative additional guide sheath for use with, for example, the additive manufacturing system of FIG. 1.

As shown in FIG. 9, the system 100 may also include an additional guide sheath 540 configured to modify or alter the jacket 118 with an additional filament material 542. For example, the additional guide sheath 540 may be positioned distal to the heating cartridge 102 (e.g., the outlet die) and may define an additional filament lumen 544 configured to receive the additional filament 542. In one or more embodiments, the additional filament 542 may be fed through the additional guide sheath 540 using the filament handling system as described herein.

The additional guide sheath 540 may be configured to move to any portion along the jacket 118 to selectively deposit additional filament material 542 on the jacket 118. For example, the additional guide sheath 540 may be configured to move relative to the jacket 118 (e.g., longitudinally or radially) using the controller. By depositing additional filament material 542 on the jacket 118, various features may be formed to modify the characteristics of the jacket 118. For example, petals or lobes may be formed on the surface of the jacket.

The additional filament 542 may include a same materials as the first filament 114. In other words, the features defined by the additional filament 542 may be the same material as the material that forms the jacket 118. In other embodiments, the additional filament 542 may include a different material than the first filament 114. In other words, the features defined by the additional filament 542 may be a different material (e.g., including different properties) than the material that forms the jacket 118.

The additional guide sheath 540 may be positioned relative to the heating cartridge (e.g., the substrate outlet port) in any suitable way. For example, in one or more embodiments, the additional guide sheath 540 may be located distal to the substrate outlet port. In other embodiments, the additional guide sheath 540 may be located proximal to the substrate outlet port (e.g., between the outlet die and the inlet die). Additionally, in one or more embodiments, the additional guide sheath 540 may be directly attached to the heat cartridge (e.g., to the outlet die). In other embodiments, the additional guide sheath 540 may be spaced apart from the heating cartridge. In such embodiments, the additional guide sheath 540 may move along with the heating cartridge to post-process the jacket after the jacket is formed.

Figure 10:
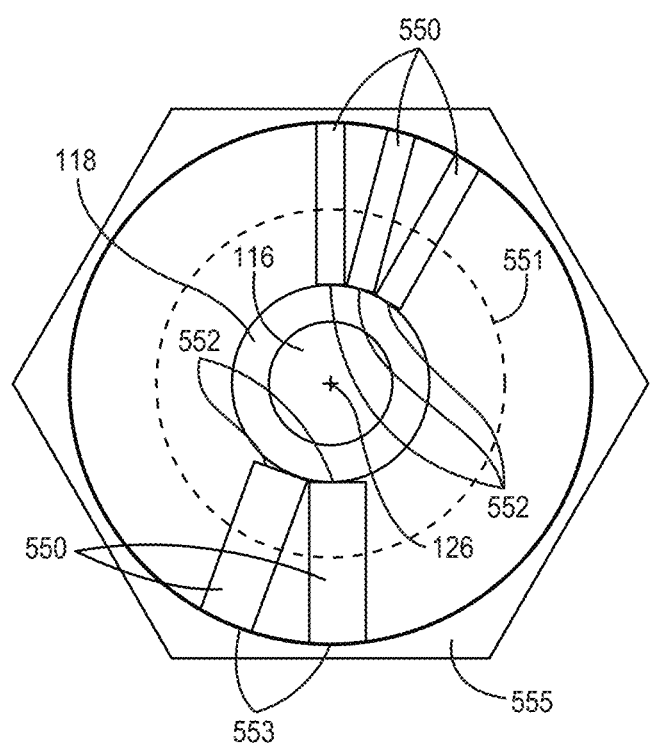
FIG. 10 is a conceptual diagram of illustrative rolling wheels for use with, for example, the additive manufacturing system of FIG. 1.

In one or more embodiments, the system 100 may include one or more rolling wheels 550 as shown in FIG. 10. The one or more rolling wheels 550 may be spaced longitudinally from the substrate outlet and engage an outer surface of the jacket 118. For example, the rolling wheels 550 may act as a surface modification tool to form the surface of the jacket 118 that may still be deformable (e.g., soft) after being melted. Each rolling wheel of the one or more rolling wheels 550 may be configured to rotate about an axis 551 perpendicular to the longitudinal axis 126. Further, the axis 551 of rotation for each rolling wheel of multiple rolling wheels 550 may be different and positioned along a circle concentric to the substrate outlet. In other words, each rolling wheel 550 may be oriented in a different plane and spaced around the jacket such that each rolling wheel is normal to the surface of the jacket 118 (e.g., an outer surface of the rolling wheel 550 may be tangential to the surface of the jacket 118). The rolling wheels 550 may be held in place using along the circular axis 551 or using clips at a distal edge 553 of each roller wheel. Each rolling wheel may define an outer surface 552 that faces the longitudinal axis 126 such that the outer surface 552 of the rolling wheel 550 may contact the surface of the jacket 118. Further, the outer surface 552 of the rolling wheel 550 may be configured to engage the jacket 118 to imprint features on the jacket 118. In one or more embodiments, the outer surface 552 of the rolling wheel 550 may define a contour that follows the curved surface of the jacket 118. Therefore, the entirety of the outer surface 552 of the rolling wheel 550 may contact the jacket 118 (e.g., to increase the amount of contact area).

The outer surface of the one or more rolling wheels 550 may define any suitable textured pattern. The textured pattern of the rolling wheel may be pressed against the jacket to imprint the inverse texture onto the jacket 118. The textured pattern of the rolling wheel may form various features onto the jacket 118 such as, e.g., channels, protrusions, dimples, bumps, etc. Each of these features imprinted onto the jacket 118 may be desirable to achieve specific characteristics of the surface of the jacket 118 as described herein. Also, the one or more rolling wheels 550 may define any suitable width. For example, the one or more rolling wheels 550 may define a width of about greater than or equal to 0.5 mm, greater than or equal to 1 mm, etc. and/or less than or equal to 2 mm, less than or equal to 1.5 mm. The width of the rolling wheel 550 may determine the amount of contact area between the rolling wheel 550 and the jacket 118.

In one or more embodiments, the rolling wheels 550 may include a radial clamp such that the width of the rolling wheel 550 may be defined as a percentage of the circumference of the jacket 118. In other words, the rolling wheels 550 may define a semi-circular shape at the outer surface 552 of the rolling wheel 550 that may be configured to engage a set amount of the jacket 118. Multiple rolling wheels may combine to encircle the circumference of the jacket 118 and modify that portion of the jacket 118. For example, in one embodiment, the system may include three rolling wheels that are positioned around the jacket 118 such that each rolling wheel 550 engages with ⅓ of the circumference of the jacket 118.

Additionally, in one or more embodiments, the system may include more than one set of rolling wheels along the axis of the jacket 118 (e.g., similar to straightening wheels). In other embodiments, the rolling wheels 550 may be arranged to shape and define curves of the jacket within the system 100 (e.g., bending the jacket 118 out of the longitudinal axis 126).

Further, in one or more embodiments, the controller may be configured to position the one or more rolling wheels 550 in an engaged position and a spaced apart position. For example, the one or more rolling wheels 550 may be configured to move towards (e.g., laterally) and in contact with the jacket 118 when in the engaged position and away from the jacket 118 when in the spaced apart position. The one or more rolling wheels 550 may move in any direction and orientation as is suitable to create a feature on the surface of the jacket 118. For example, in one embodiment, the rolling wheels 550 may move rotationally about the longitudinal axis around the jacket 118.

The one or more rolling wheels 550 may include any number of suitable rolling wheels. For example, the one or more rolling wheels 550 may include one, two, three, or four or more rolling wheels. In one or more embodiments, multiple rolling wheels 550 may be equally spaced apart. In other embodiments, multiple rolling wheels 550 may be adjacent to one another. In one or more embodiments, the multiple rolling wheels 550 may be configured to move independently from one another.

The one or more rolling wheels 550 may be positioned relative to the heating cartridge (e.g., the substrate outlet port) in any suitable way. For example, in one or more embodiments, the one or more rolling wheels 550 may be located distal to the substrate outlet port. In other embodiments, the one or more rolling wheels 550 may be located proximal to the substrate outlet port (e.g., between the outlet die and the inlet die). Additionally, in one or more embodiments, the one or more rolling wheels 550 may be directly attached to the heat cartridge (e.g., to the outlet die 555). In other embodiments, the one or more rolling wheels 550 may be spaced apart from the heating cartridge. In such embodiments, the one or more rolling wheels 550 may move along with the heating cartridge to post-process the jacket after the jacket is formed.

Figure 13:
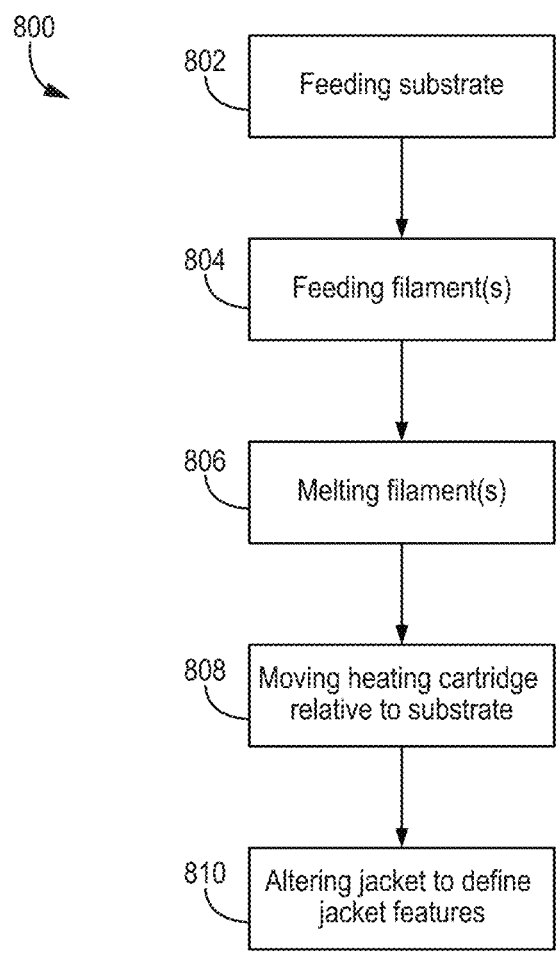
FIG. 13 is a flow diagram that illustrates one example of a method for use with, for example, the additive manufacturing system of FIG. 1.

FIG. 13 shows one example of a method 800 of using the system 100 (FIG. 1) for additive manufacturing. The method 800 may be used to manufacture an implantable medical device.

The method 800 may include feeding the substrate 802, for example, through a substrate channel in a heating cartridge. The substrate channel may be in fluid communication with an interior cavity of the heating cartridge.

The method 800 may include feeding one or more filaments 804. For example, at least a first filament may be fed through a filament port of the heating cartridge into the interior cavity. In some embodiments, a second filament may be fed through another filament port into the interior cavity.

The method 800 may include melting one or more of the filaments 806, for example, in the interior cavity. Any portion of the filaments contained in the interior cavity may be melted. In some embodiments, a second filament is melted with the first filament.

The method 800 may include moving the heating cartridge relative to the substrate 808, for example, at least in a longitudinal direction to form a jacket comprising material from at least the first filament. The heating cartridge or substrate may also be rotated relative to one another. The jacket may be formed from material of at least the first filament. In some embodiments, the jacket may be formed from material of at least the first filament and the second filament.

The method 800 may also include altering the jacket 810 to define jacket features. These jacket features may include any suitable feature as described herein to modify the characteristics of the medical device being formed. For example, the jacket features may allow for interfacing with specific geometries and anatomical features. In other words, the jacket features may allow for controlling friction interfaces as well as create fixation or anchoring components on the external surface of the jacket body (e.g., such that the jacket features may accomplish various "jobs"). Further, the jacket features may assist in holding the medical device steady during device movement, may provide visual markers, or may adjust the mechanical properties of the device.

The jacket features may take the shape of various forms. For example, in one or more embodiments, the jacket features may include threads of differing/variable pitch added to the surface of the jacket. In one or more embodiments, the jacket features may include longitudinal splines added to the external surface of the jacket, e.g., as described in U.S. Pat. App. No. 63/001,832, entitled "3D PRINTED SPLINES ON MEDICAL DEVICES AND METHODS TO MANUFACTURE THE SAME," which is herein incorporated by reference. In one or more embodiments, the jacket features may include elongated structures added to the surface of the jacket to, e.g., change the general shape profile (e.g., wings or two lobed, a triangle, a box/cube, etc.) of the jacket. In one or more embodiments, the jacket features may include intermittent surface elevations (e.g., non-continuous changes in thickness/diameter). In one or more embodiments, the jacket features may include a varying output geometry (e.g., a taper) of an outer surface of the jacket.

These externally added three-dimensional surface features of the jacket, as described herein, may aid in performance of a medical device or delivery system by, e.g., modifying the friction of interface surfaces between the medical device body and the anatomy of the patient, creating anchoring mechanisms for screwing or threading the medical device into an annular/cylindrical anatomical feature, or creating preferential performance characteristics (e.g., bending, straightening, torque, etc.).

Furthermore, these jacket features may be formed by any suitable tools. For example, the tools and process herein may provide a way to design and develop medical device features and methods of making the same. Specifically, as described herein, the jacket may be altered by adjusting the shaped and/or size of the jacket using a shutter, the jacket may be altered by trimming a portion of the jacket using one or more cutting tools, the jacket may be altered by depositing an additional filament on the jacket using an additional guide sheath, the jacket may be altered by imprinting a texture onto the jacket using one or more rolling wheels, etc.

Further, in some embodiments, the method 800 may also include adjusting a ratio of the first filament relative to the second filament over a longitudinal distance to change the Shore durometer of the catheter jacket over the longitudinal distance.

Figure 14:
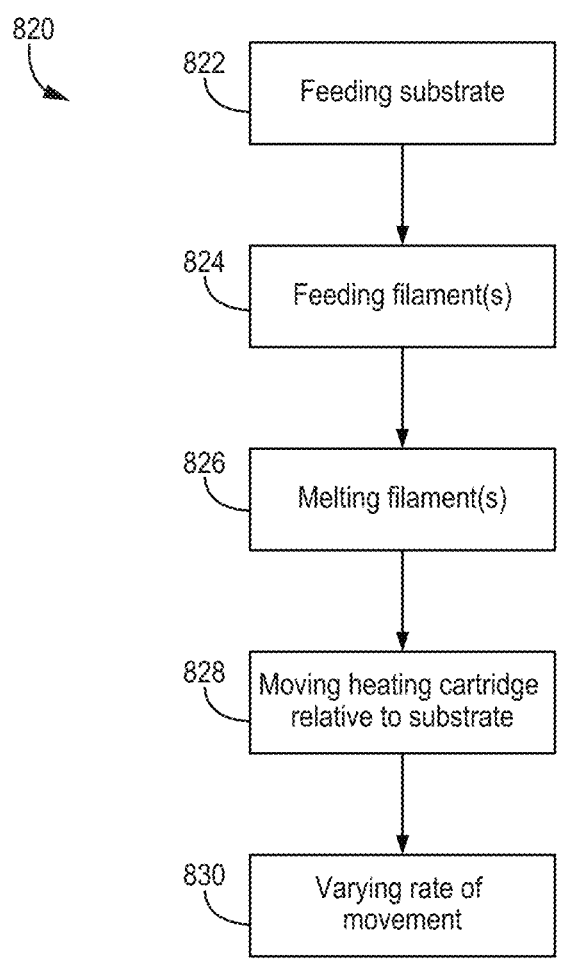
FIG. 14 is a flow diagram that illustrates another example of a method for use with, for example, the additive manufacturing system of FIG. 1.

FIG. 14 shows another example of a method 820 of using the system 100 (FIG. 1) for additive manufacturing. The method 820 may be used to manufacture an implantable medical device.

The method 820 may include feeding the substrate 822, for example, through a substrate channel in a heating cartridge. The substrate channel may be in fluid communication with an interior cavity of the heating cartridge.

The method 820 may include feeding one or more filaments 824. For example, at least a first filament may be fed through a filament port of the heating cartridge into the interior cavity. In some embodiments, a second filament may be fed through another filament port into the interior cavity.

The method 820 may include melting one or more of the filaments 826, for example, in the interior cavity. Any portion of the filaments contained in the interior cavity may be melted. In some embodiments, a second filament is melted with the first filament.

The method 820 may include moving the heating cartridge relative to the substrate 828, for example, at least in a longitudinal direction to form a jacket comprising material from at least the first filament. The heating cartridge or substrate may also be rotated relative to one another. The jacket may be formed from material of at least the first filament. In some embodiments, the jacket may be formed from material of at least the first filament and the second filament.

Figure 11:
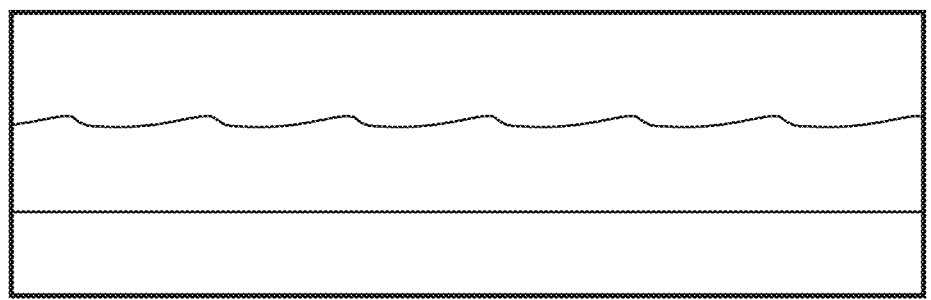
FIG. 11 is an image of an illustrative catheter including circumferential protrusions that may be manufactured using the additive manufacturing system of FIG. 1.
Figure 12:
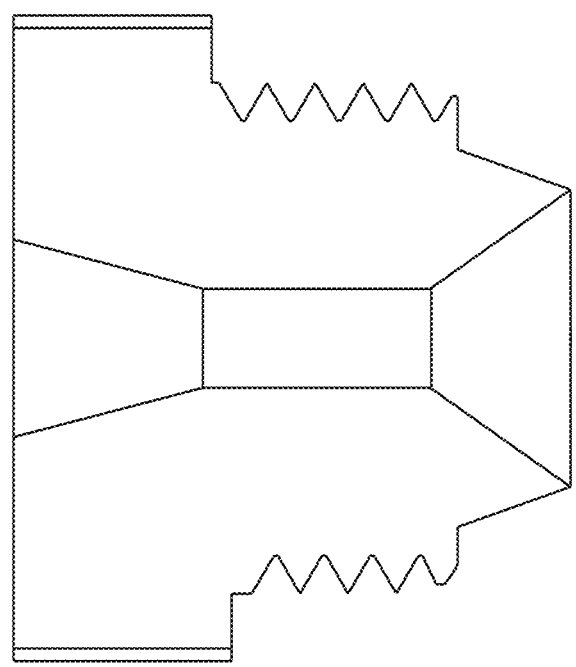
FIG. 12 is an image of an illustrative heating cartridge for use with, for example, the additive manufacturing system of FIG. 1.

The method 820 may also include varying the rate of movement 830 between the heating cartridge and the substrate to define jacket features. For example, the controller may be configured to vary the longitudinal speed of the substrate relative to the heating cartridge. By varying the speed of movement of these components relative to one another during the formation of the jacket, the thickness of the jacket may change over the longitudinal distance. As a result, the jacket may define circumferential protrusions extending from an outer surface of the jacket, e.g., as shown in FIG. 11. These intermittent changes in surface elevations of the jacket may provide varying characteristics to the jacket as described herein. Additionally, in one or more embodiments, the controller may vary the longitudinal speed of the substrate relative to the heating cartridge to define a taper of an outer surface of the jacket. Specifically, in one example, the taper may modify the jacket thickness from 9 French to 7 French. Further, in one or more embodiments, the system may include the heating cartridge (e.g., a tunnel die) illustrated in FIG. 12 to provide a taper while using varying longitudinal speeds.

Further, in some embodiments, the method 820 may also include adjusting a ratio of the first filament relative to the second filament over a longitudinal distance to change the Shore durometer of the catheter jacket over the longitudinal distance.

Figure 15:
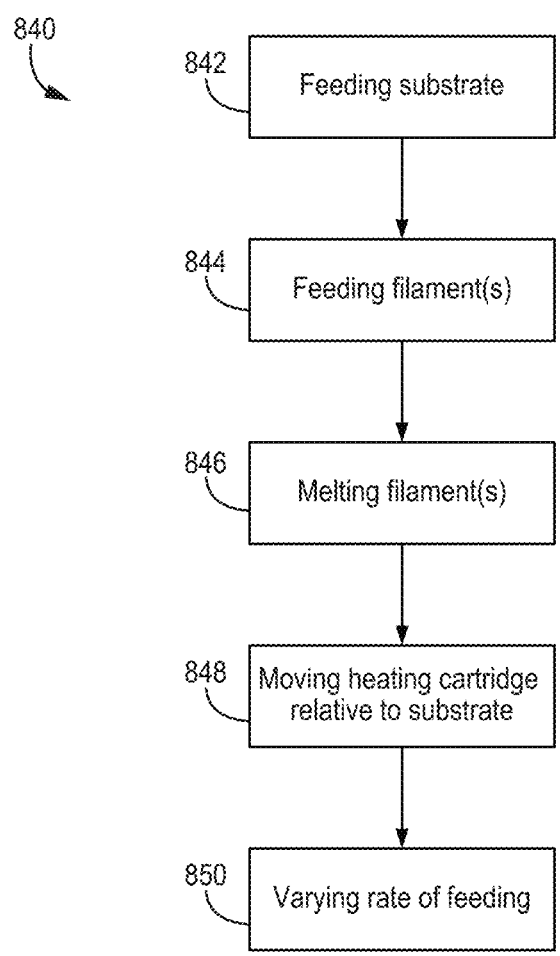
FIG. 15 is a flow diagram that illustrates yet another example of a method for use with, for example, the additive manufacturing system of FIG. 1.

FIG. 15 shows yet another example of a method 840 of using the system 100 (FIG. 1) for additive manufacturing. The method 840 may be used to manufacture an implantable medical device.

The method 840 may include feeding the substrate 842, for example, through a substrate channel in a heating cartridge. The substrate channel may be in fluid communication with an interior cavity of the heating cartridge.

The method 840 may include feeding one or more filaments 844. For example, at least a first filament may be fed through a filament port of the heating cartridge into the interior cavity. In some embodiments, a second filament may be fed through another filament port into the interior cavity.

The method 840 may include melting one or more of the filaments 846, for example, in the interior cavity. Any portion of the filaments contained in the interior cavity may be melted. In some embodiments, a second filament is melted with the first filament.

The method 840 may include moving the heating cartridge relative to the substrate 848, for example, at least in a longitudinal direction to form a jacket comprising material from at least the first filament. The heating cartridge or substrate may also be rotated relative to one another. The jacket may be formed from material of at least the first filament. In some embodiments, the jacket may be formed from material of at least the first filament and the second filament.

The method 840 may also include varying the rate of feeding 850 the first filament through the filament port to define a jacket features. For example, the controller may be configured to vary the feeding force applied to the one or more filaments. By varying the feeding force of the one or more filaments during the formation of the jacket, the thickness of the jacket may change over the longitudinal distance. As a result, the jacket may define circumferential protrusions extending from an outer surface of the jacket, e.g., as shown in FIG. 11. These intermittent changes in surface elevations of the jacket may provide varying characteristics to the jacket as described herein. Additionally, in one or more embodiments, the controller may vary the feeding force applied to one or more filaments to define a taper of an outer surface of the jacket. Specifically, in one example, the taper may modify the jacket thickness from 9 French to 7 French. Further, in one or more embodiments, the system may include the heating cartridge illustrated in FIG. 12 to provide a taper while using varying feeding forces.

Further, in some embodiments, the method 820 may also include adjusting a ratio of the first filament relative to the second filament over a longitudinal distance to change the Shore durometer of the catheter jacket over the longitudinal distance.

ILLUSTRATIVE EMBODIMENTS

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

A1. An additive manufacturing apparatus comprising:
  a heating block at least partially defining an interior volume to allow an elongate substrate to pass through the interior volume and through the heating block, wherein the heating block at least partially defines a first filament port in fluid communication with the interior volume;
  a first guide sheath coupled to the heating block and extending into the first filament port from an exterior of the heating block, the first guide sheath defining a lumen in fluid communication with the interior volume; and
  an outlet die located proximate a distal side of the heating block and at least partially defining the interior volume, wherein outlet die at least partially defines a substrate outlet for the elongate substrate, wherein the substrate outlet is adapted to be selectively adjusted to modify the size and/or shape of the substrate outlet.

A2. The apparatus according to embodiment A1, further comprising a shutter defining an opening spaced longitudinally from the substrate outlet, wherein the shutter comprises a body portion and one or more fins movably coupled to the body portion such that the one or more fins are adapted to move relative to the substrate outlet to modify the size and/or shape of the substrate outlet.

A3. The apparatus according to embodiment A2, wherein each of the one or more fins extends between a first end region movably coupled to the body portion and a second end region adapted to move relative to the substrate outlet.

A4. The apparatus according to embodiment A3, wherein the shutter further comprises one or more linkage, wherein each linkage corresponds to a fin of the one or more fins, wherein each linkage extends between a first end region movably coupled to the body portion and a second end region movably coupled to the corresponding fin, wherein body portion defines one or more slots within which each linkage is movably coupled.

A5. The apparatus according to embodiment A2, wherein the shutter is located distal to the substrate outlet.

A6. The apparatus according to embodiment A2, wherein the shutter is located proximal to the substrate outlet.

A7. The apparatus according to embodiment A2, wherein the shutter is directly attached to the outlet die.

A8. The apparatus according to embodiment A2, wherein the shutter is spaced apart from the outlet die.

A9. The apparatus according to any preceding A embodiment, further comprising an inlet die at least partially defining a substrate inlet port, wherein the interior volume is at least partially defined by the inlet die coupled to a proximal side of the heating block.

A10. The apparatus according to any preceding A embodiment, wherein the substrate outlet port defines one, two, three, four, or more cutouts.

A11. The apparatus according to any preceding A embodiment, wherein the substrate outlet port defines one, two, three, four, or more protrusions.

A12. The apparatus according to any preceding A embodiment, wherein the heating block at least partially defines a second filament port in fluid communication with the interior volume.

A13. The apparatus according to any preceding A embodiment, further comprising one or more heating elements thermally coupled to the heating block to melt filament material in the interior volume.

B1. An additive manufacturing system comprising:
  a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament;
  a heating element thermally coupled to the heating cartridge to heat the interior volume;
  a filament handling system comprising one or more motors to feed at least a first filament through the first filament port into the interior volume;
  a substrate handling system comprising:
    a head stock comprising a distal clamp to secure a distal portion of an elongate substrate, wherein the substrate is positioned to pass through the substrate channel when secured by the head stock; and
    one or more motors to translate or rotate one or both of the substrate when secured by the headstock and the heating cartridge relative to one another;
  a controller operably coupled to the heating element, one or more motors of the filament handling system, and one or more motors of the substrate handling system, the controller configured to:
    activate the heating element to melt any portion of the first filament in the interior volume;
    control the one or more motors of the filament handling system to selectively control the feeding of the first filament into the interior volume; and
    control one or more motors of the substrate handling system to move one or both of the substrate and the heating cartridge relative to one another in at least a longitudinal direction to form an elongate catheter jacket around the substrate, wherein the catheter jacket comprises material from the first filament; and a shutter comprising a body portion defining a channel spaced longitudinally from the substrate outlet port of the heating cartridge, wherein the shutter is adapted to be selectively adjusted to modify the size and/or shape of the substrate outlet port and engage the catheter jacket.

B2. The system according to embodiment B1, wherein the shutter further comprises one or more fins movably coupled to the body portion such that the one or more fins are configured to move relative to the substrate outlet port to modify the size and/or shape of the substrate outlet port.

B3. The system according to embodiment B2, wherein each of the one or more fins extends between a first end region movably coupled to the body portion and a second end region adapted to move relative to the substrate outlet.

B4. The system according to embodiment B3, wherein the shutter further comprises one or more linkage, wherein each linkage corresponds to a fin of the one or more fins, wherein each linkage extends between a first end region movably coupled to the body portion and a second end region movably coupled to the corresponding fin, wherein body portion defines one or more slots within which each linkage is movably coupled.

B5. The system according to embodiment B2, wherein the shutter is located distal to the substrate outlet port.

B6. The system according to embodiment B2, wherein the shutter is located proximal to the substrate outlet port.

B7. The system according to embodiment B2, wherein the shutter is directly attached to the heating cartridge.

B8. The system according to embodiment B2, wherein the shutter is spaced apart from the heating cartridge.

B9. The system according to any preceding B embodiment, wherein the heating cartridge further comprises a second filament port in fluid communication with the interior volume, wherein the one or more motors of the filament handling system are adapted to feed a second filament through the second filament port into the interior volume, wherein the controller is configured to:

activate the heating element to melt any portion of the second filament in the interior volume control the one or more motors of the filament handling system to selectively control the feeding of the second filament into the interior volume, wherein the catheter jacket comprises material from at least one of the first filament and the second filament B10. The system according to any preceding B embodiment, wherein the heating cartridge comprises an inlet die, an outlet die, and a heating block, wherein heating block defines the first filament port and the second filament port.

B11. The system according to any preceding B embodiment, wherein one or both of the substrate inlet port and the substrate outlet port defines one, two, three, four, or more cutouts, and the controller is configured to rotate the substrate relative to the heating cartridge while translating the substrate relative to the heating cartridge to form the elongate catheter jacket around the substrate.

B12. The system according to embodiment B11, wherein the substrate outlet port defines the one, two, three, four, or more cutouts and the catheter jacket comprises a number of helical protrusions corresponding to the number of cutouts.

B13. The system according to any preceding B embodiment, wherein one or both of the substrate inlet port and the substrate outlet port defines one, two, three, four, or more protrusions.

B14. The system according to embodiment B13, wherein the substrate outlet port includes the one, two, three, four, or more protrusions and the catheter jacket comprises a corresponding number of channels.

B15. The system according to any preceding B embodiment, wherein the controller is configured to move the head stock in at least the longitudinal direction away from the heating cartridge to form the catheter jacket.

B16. The system according to any preceding B embodiment, wherein the substrate handling system comprises a tail stock comprising a proximal clamp to secure a proximal portion of the substrate.

B17. The system according to embodiment B16, wherein the controller is configured to move the heating cartridge in at least the longitudinal direction away from the head stock to form the catheter jacket.

B18. The system according to any preceding B embodiment, further comprising the substrate, wherein the substrate comprises a lubricious coating, a liner, and a braid, and the catheter jacket is formed around the braid.

C1. An additive manufacturing apparatus comprising:

a heating block at least partially defining an interior volume to allow an elongate substrate to pass through the interior volume and through the heating block along a longitudinal axis, wherein the heating block at least partially defines a first filament port in fluid communication with the interior volume;

a first guide sheath coupled to the heating block and extending into the first filament port from an exterior of the heating block, the first guide sheath defining a lumen in fluid communication with the interior volume;

an outlet die located proximate a distal side of the heating block and at least partially defining the interior volume, wherein outlet die at least partially defines a substrate outlet for the elongate substrate; and one or more cutting tools spaced longitudinally from the substrate outlet, wherein each cutting tool of the one or more cutting tools comprises a cutting edge oriented towards the longitudinal axis.

C2. The apparatus according to any preceding C embodiment, wherein each cutting tool of the one or more cutting tools extends between a base edge and the cutting edge along a cutting axis, wherein the cutting axis positioned at an angle to the longitudinal axis of less than or equal to about 45 degrees.

C3. The apparatus according to any preceding C embodiment, wherein the one or more cutting tools are movably coupled to the outlet die.

C4. The apparatus according to any preceding C embodiment, wherein the one or more cutting tools are configured to move between an engaged position and a spaced apart position.

C5. The apparatus according to any preceding C embodiment, wherein the cutting edge is positioned between an edge of the substrate outlet and the longitudinal axis.

C6. The apparatus according to any preceding C embodiment, wherein the one or more cutting tools comprises one, two, three, or four cutting tools.

C7. The apparatus according to any preceding C embodiment, wherein the one or more cutting tools are located distal to the substrate outlet.

C8. The apparatus according to embodiments C1-C6, wherein the one or more cutting tools are located proximal to the substrate outlet.

C9. The apparatus according to any preceding C embodiment, wherein the one or more cutting tools are directly attached to the outlet die.

C10. The apparatus according to embodiments C1-C8, wherein the one or more cutting tools are spaced apart from the outlet die.

D1. An additive manufacturing system comprising:
- a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament;
- a heating element thermally coupled to the heating cartridge to heat the interior volume;
- a filament handling system comprising one or more motors to feed at least a first filament through the first filament port into the interior volume;
- a substrate handling system comprising:
  - a head stock comprising a distal clamp to secure a distal portion of an elongate substrate, wherein the substrate is positioned to pass through the substrate channel along a longitudinal axis when secured by the head stock; and
  - one or more motors to translate or rotate one or both of the substrate when secured by the headstock and the heating cartridge relative to one another;
- a controller operably coupled to the heating element, one or more motors of the filament handling system, and one or more motors of the substrate handling system, the controller configured to:
  - activate the heating element to melt any portion of the first filament in the interior volume;
  - control the one or more motors of the filament handling system to selectively control the feeding of the first filament into the interior volume; and
  - control one or more motors of the substrate handling system to move one or both of the substrate and the heating cartridge relative to one another in at least a longitudinal direction to form an elongate catheter jacket around the substrate, wherein the catheter jacket comprises material from the first filament; and
- one or more cutting tools spaced longitudinally from the substrate outlet port of the heating cartridge, wherein each cutting tool of the one or more cutting tools comprises a cutting edge oriented towards the longitudinal axis and configured to selectively engage the catheter jacket.

D2. The system according to any preceding D embodiment, wherein each cutting tool of the one or more cutting tools extends between a base edge and the cutting edge along a cutting axis, wherein the cutting axis positioned at an angle to the longitudinal axis of less than or equal to about 45 degrees.

D3. The system according to any preceding D embodiment, wherein the one or more cutting tools are movably coupled to the heating cartridge.

D4. The system according to any preceding D embodiment, wherein the one or more cutting tools are configured to move between an engaged position and a spaced apart position.

D5. The system according to any preceding D embodiment, wherein the cutting edge is positioned between an edge of the substrate outlet and the longitudinal axis.

D6. The system according to any preceding D embodiment, wherein the one or more cutting tools comprises one, two, three, or four cutting tools.

D7. The system according to any preceding D embodiment, wherein the one or more cutting tools are located distal to the substrate outlet port.

D8. The system according to embodiments D1-D6, wherein the one or more cutting tools are located proximal to the substrate outlet port D9. The system according to any preceding D embodiment, wherein the one or more cutting tools are directly attached to the heating cartridge.

D10. The system according to embodiments D1-D8, wherein the one or more cutting tools are spaced apart from the heating cartridge.

E1. An additive manufacturing apparatus comprising:
- a heating block at least partially defining an interior volume to allow an elongate substrate to pass through the interior volume and through the heating block along a longitudinal axis, wherein the heating block at least partially defines a first filament port in fluid communication with the interior volume;
- a first guide sheath coupled to the heating block and extending into the first filament port from an exterior of the heating block, the first guide sheath defining a lumen in fluid communication with the interior volume;
- an outlet die located proximate a distal side of the heating block and at least partially defining the interior volume, wherein outlet die at least partially defines a substrate outlet for the elongate substrate; and
- an additional guide sheath distal the outlet die and defining an additional filament lumen configured to receive an additional filament.

E2. The apparatus according to any preceding E embodiment, wherein the additional guide sheath is directly attached to the outlet die.

E3. The apparatus according to embodiment E1, wherein the additional guide sheath is spaced apart from the outlet die.

F1. An additive manufacturing system comprising:
- a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament;
- a heating element thermally coupled to the heating cartridge to heat the interior volume;
- a filament handling system comprising one or more motors to feed at least a first filament through the first filament port into the interior volume;
- a substrate handling system comprising:
  - a head stock comprising a distal clamp to secure a distal portion of an elongate substrate, wherein the substrate is positioned to pass through the substrate channel along a longitudinal axis when secured by the head stock; and
  - one or more motors to translate or rotate one or both of the substrate when secured by the headstock and the heating cartridge relative to one another;
- a controller operably coupled to the heating element, one or more motors of the filament handling system, and one or more motors of the substrate handling system, the controller configured to:
  - activate the heating element to melt any portion of the first filament in the interior volume;

control the one or more motors of the filament handling system to selectively control the feeding of the first filament into the interior volume; and control one or more motors of the substrate handling system to move one or both of the substrate and the heating cartridge relative to one another in at least a longitudinal direction to form an elongate catheter jacket around the substrate, wherein the catheter jacket comprises material from the first filament; and an additional guide sheath distal the heating block and defining an additional filament lumen configured to receive an additional filament, wherein the additional guide sheath is configured to selectively deposit the additional filament on the catheter jacket.

F2. The system according to any preceding F embodiment, wherein the additional guide sheath is directly attached to the heating cartridge.

F3. The system according to embodiment F1, wherein the additional guide sheath is spaced apart from the heating cartridge.

F4. The system according to any preceding F embodiment, wherein the additional guide sheath is configured to move relative to the elongate substrate.

F5. The system according to any preceding F embodiment, wherein the additional filament comprises a same material as the first filament.

F6. The system according to any preceding F embodiment, wherein the additional filament comprises a different material than the first filament.

F7. The system according to any preceding F embodiment, wherein the additional filament lumen comprises multiple ports through which the additional filament is deposited on the catheter jacket.

G1. An additive manufacturing apparatus comprising:
a heating block at least partially defining an interior volume to allow an elongate substrate to pass through the interior volume and through the heating block along a longitudinal axis, wherein the heating block at least partially defines a first filament port in fluid communication with the interior volume;
a first guide sheath coupled to the heating block and extending into the first filament port from an exterior of the heating block, the first guide sheath defining a lumen in fluid communication with the interior volume;
an outlet die located proximate a distal side of the heating block and at least partially defining the interior volume, wherein outlet die at least partially defines a substrate outlet for the elongate substrate; and
one or more rolling wheels spaced longitudinally from the substrate outlet, wherein each rolling wheel of the one or more rolling wheels is configured to rotate about an axis perpendicular to the longitudinal axis and defines an outer surface facing the longitudinal axis.

G2. The apparatus according to any preceding G embodiment, wherein each rolling wheel of the one or more rolling wheels define a width of about 1 mm.

G3. The apparatus according to any preceding G embodiment, wherein the outer surface of the one or more rolling wheels define a textured pattern.

G4. The apparatus according to any preceding G embodiment, wherein the one or more rolling wheels are configured to move laterally between an engaged position and a spaced apart position.

G5. The apparatus according to any preceding G embodiment, wherein the one or more rolling wheels comprises one, two, three, or four rolling wheels.

G6. The apparatus according to any preceding G embodiment, wherein the one or more rolling wheels are located distal to the substrate outlet.

H1. An additive manufacturing system comprising:
a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament;
a heating element thermally coupled to the heating cartridge to heat the interior volume;
a filament handling system comprising one or more motors to feed at least a first filament through the first filament port into the interior volume;
a substrate handling system comprising:
a head stock comprising a distal clamp to secure a distal portion of an elongate substrate, wherein the substrate is positioned to pass through the substrate channel along a longitudinal axis when secured by the head stock; and
one or more motors to translate or rotate one or both of the substrate when secured by the headstock and the heating cartridge relative to one another;
a controller operably coupled to the heating element, one or more motors of the filament handling system, and one or more motors of the substrate handling system, the controller configured to:
activate the heating element to melt any portion of the first filament in the interior volume;
control the one or more motors of the filament handling system to selectively control the feeding of the first filament into the interior volume; and
control one or more motors of the substrate handling system to move one or both of the substrate and the heating cartridge relative to one another in at least a longitudinal direction to form an elongate catheter jacket around the substrate, wherein the catheter jacket comprises material from the first filament; and
one or more rolling wheels spaced longitudinally from the substrate outlet port of the heating cartridge, wherein each rolling wheel of the one or more rolling wheels is configured to rotate about an axis perpendicular to the longitudinal axis and defines an outer surface configured to engage the catheter jacket to imprint features thereon.

H2. The system according to any preceding H embodiment, wherein each rolling wheel of the one or more rolling wheels define a width of about 1 mm.

H3. The system according to any preceding H embodiment, wherein the outer surface of the one or more rolling wheels define a textured pattern.

H4. The system according to any preceding H embodiment, wherein the one or more rolling wheels are configured to move laterally between an engaged position and a spaced apart position.

H5. The system according to any preceding H embodiment, wherein the one or more rolling wheels comprises one, two, three, or four rolling wheels.

H6. The system according to any preceding H embodiment, wherein the one or more rolling wheels are located distal to the substrate outlet port.

I1. A method for additive manufacturing of an implantable medical device, the method comprising:

feeding a substrate through a substrate channel in a heating cartridge, the substrate channel in fluid communication with an interior cavity of the heating cartridge;

feeding at least a first filament through a filament port into the interior cavity;

melting the first filament in the interior cavity;

moving the heating cartridge relative to the substrate at least in a longitudinal direction to form a jacket comprising material from at least the first filament; and altering the jacket to define jacket features.

I2. The method according to embodiment I1, wherein altering the catheter jacket comprises adjusting the shape and/or size of the catheter jacket using a shutter.

I3. The method according to embodiment I1, wherein altering the catheter jacket comprises trimming a portion of the catheter jacket using one or more cutting tools.

I4. The method according to embodiment I1, wherein altering the catheter jacket comprises depositing an additional filament on the catheter jacket using an additional guide sheath.

I5. The method according to embodiment I1, wherein altering the catheter jacket comprises imprinting a texture onto the catheter jacket using one or more rolling wheels.

I6. The method according to any preceding I embodiment, wherein the catheter jacket features comprise a taper of an outer surface of the catheter jacket.

I7. The method according to any preceding I embodiment, wherein the catheter jacket features comprise circumferential protrusions extending from an outer surface of the catheter jacket.

I8. The method according to any preceding I embodiment, wherein the catheter jacket features comprise variable splines extending from an outer surface of the catheter jacket.

I9. The method according to any preceding I embodiment, further comprising:

feeding a second filament through another filament port into the interior cavity; and melting the second filament with the first filament to form the catheter jacket comprising material from at least the first filament and the second filament I10. The method according to embodiment I9, further comprising adjusting a ratio of the first filament relative to the second filament over a longitudinal distance to change the Shore durometer of the catheter jacket over the longitudinal distance.

J1. A method for additive manufacturing of an implantable medical catheter, the method comprising:

feeding a substrate through a substrate channel in a heating cartridge, the substrate channel in fluid communication with an interior cavity of the heating cartridge;

feeding at least a first filament through a filament port into the interior cavity;

melting the first filament in the interior cavity;

moving the heating cartridge relative to the substrate at least in a longitudinal direction to form a catheter jacket comprising material from at least the first filament; and varying the rate of movement between the heating cartridge and the substrate to define catheter jacket features.

J2. The method according to embodiment J1, wherein the catheter jacket features comprise a taper of an outer surface of the catheter jacket J3. The method according to embodiment J1, wherein the catheter jacket features comprise circumferential protrusions extending from an outer surface of the catheter jacket.

K1. A method for additive manufacturing of an implantable medical catheter, the method comprising:

feeding a substrate through a substrate channel in a heating cartridge, the substrate channel in fluid communication with an interior cavity of the heating cartridge;

feeding at least a first filament through a filament port into the interior cavity;

melting the first filament in the interior cavity;

moving the heating cartridge relative to the substrate at least in a longitudinal direction to form a catheter jacket comprising material from at least the first filament; and varying the rate of feeding the first filament through the filament port to define catheter jacket features.

K2. The method according to embodiment K1, wherein the catheter jacket features comprise a taper of an outer surface of the catheter jacket K3. The method according to embodiment K1, wherein the catheter jacket features comprise circumferential protrusions extending from an outer surface of the catheter jacket.

Thus, various embodiments described herein are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

The invention claimed is:

1. An additive manufacturing apparatus comprising:
a heating block extending between a proximal side and a distal side and comprising a substrate inlet proximate the proximal side and a substrate outlet proximate the distal side, the heating block at least partially defining an interior volume to allow an elongate substrate to pass through the interior volume and through the heating block between the substrate inlet and the substrate outlet, wherein the heating block at least partially defines a first filament port in fluid communication with the interior volume, wherein the first filament port is different than the substrate inlet and the substrate outlet;
a first guide sheath coupled to the heating block and extending into the first filament port from an exterior of the heating block, the first guide sheath defining a lumen in fluid communication with the interior volume;
an outlet die located proximate the distal side of the heating block and at least partially defining the interior volume, wherein outlet die at least partially defines the substrate outlet for the elongate substrate, wherein the substrate outlet is adapted to be selectively adjusted to modify a size and/or shape of the substrate outlet, and wherein the outlet die defines one or more cutouts; and
a shutter defining an opening spaced longitudinally from the substrate outlet, wherein the shutter comprises a body portion and one or more fins movably coupled to the body portion such that the one or more fins are adapted to move relative to the outlet die to modify the size and/or shape of the substrate outlet, and wherein the one or more fins of the shutter are further adapted to move to modify a size and/or shape of the one or more cutouts of the outlet die.

2. The apparatus of claim 1, wherein each of the one or more fins extends between a first end region movably coupled to the body portion and a second end region adapted to move relative to the substrate outlet.

3. The apparatus of claim 2, wherein the shutter further comprises one or more linkage, wherein each linkage corresponds to a fin of the one or more fins, wherein each linkage extends between a first end region movably coupled to the body portion and a second end region movably coupled to the corresponding fin, wherein body portion defines one or more slots within which each linkage is movably coupled.

4. The apparatus of claim 1, wherein the shutter is located distal to the substrate outlet.

5. The apparatus of claim 1, wherein the shutter is located proximal to the substrate outlet.

6. The apparatus of claim 1, wherein the shutter is directly attached to the outlet die.

7. The apparatus of claim 1, wherein the heating block at least partially defines a second filament port in fluid communication with the interior volume.

8. An additive manufacturing apparatus comprising:
a heating block at least partially defining an interior volume to allow an elongate substrate to pass through the interior volume and through the heating block, wherein the heating block at least partially defines a first filament port in fluid communication with the interior volume;
a first guide sheath coupled to the heating block and extending into the first filament port from an exterior of the heating block, the first guide sheath defining a lumen in fluid communication with the interior volume;
an outlet die located proximate a distal side of the heating block and at least partially defining the interior volume, wherein outlet die at least partially defines a substrate outlet for the elongate substrate, wherein the substrate outlet is adapted to be selectively adjusted to modify a size and/or shape of the substrate outlet; and
a shutter defining an opening spaced longitudinally from the substrate outlet, wherein the shutter comprises:
a body portion,
one or more fins movably coupled to the body portion such that the one or more fins are adapted to move relative to the outlet die to modify the size and/or shape of the substrate outlet, wherein each of the one or more fins extends between a first end region movably coupled to the body portion and a second end region adapted to move relative to the substrate outlet, and
one or more linkage, wherein each linkage corresponds to a fin of the one or more fins, wherein each linkage extends between a first end region movably coupled to the body portion and a second end region movably coupled to the corresponding fin, wherein body portion defines one or more slots within which each linkage is movably coupled.

9. The apparatus of claim 8, wherein the shutter is located distal to the substrate outlet.

10. The apparatus of claim 8, wherein the shutter is located proximal to the substrate outlet.

11. The apparatus of claim 8, wherein the shutter is directly attached to the outlet die.

12. The apparatus of claim 8, wherein the heating block at least partially defines a second filament port in fluid communication with the interior volume.

\* \* \* \* \*